United States Patent [19]
Moreland et al.

[11] Patent Number: 5,241,078
[45] Date of Patent: Aug. 31, 1993

[54] COUPLING AGENTS AND STERICALLY HINDERED DISULFIDE LINKED CONJUGATES PREPARED THEREFROM

[75] Inventors: Margaret Moreland, Berkeley; I. Lawrence Greenfield, Pleasant Hill; Danute E. Nitecki, Berkeley, all of Calif.

[73] Assignee: Cetus Oncology, Emeryville, Calif.

[21] Appl. No.: 837,678

[22] Filed: Feb. 14, 1992

Related U.S. Application Data

[63] Continuation of Ser. No. 206,573, Jun. 14, 1988, abandoned.

[51] Int. Cl.$^5$ .................. C07D 207/46; C07C 321/04
[52] U.S. Cl. .................................... 548/542; 558/254; 564/500; 564/501
[58] Field of Search ................ 564/500, 501; 548/542; 558/254

[56] References Cited

U.S. PATENT DOCUMENTS

| | | | |
|---|---|---|---|
| 4,340,535 | 7/1982 | Voisin et al. | 260/112 B |
| 4,350,626 | 9/1982 | Masuho et al. | 260/112.5 R |
| 4,357,273 | 11/1982 | Masuho et al. | 260/112.5 B |
| 4,450,154 | 5/1984 | Masuho et al. | 260/112 R |
| 4,543,211 | 9/1985 | Kato et al. | 260/112 B |
| 4,638,049 | 1/1987 | Masuho et al. | 530/388 |
| 4,880,935 | 11/1989 | Thorpe | 548/542 |

OTHER PUBLICATIONS

Bodanszky, M., "The Peptides", 1:105-196 (Gross & Meienhofer Eds.), Academic Press, 1979.
Greene, T., 1977, Annual Review of Biochemistry, 46:193-217.
Peters, K., et al., 1977, Annual Review of Biochemistry, 46:523-551.
Pearson, J. W., et al., 1989, Cancer Research, 49:3562-3567.
Siena, S., et al., 1989, Cancer Research, 49:3328-3332.
Weiner, L. M., et al., 1989, Cancer Research, 49:4062-4067.
Vitetta et al., 1987, Science, 238:1098-1104.
Imperial Cancer Research Fund Patents Ltd. (PATCO), Technology Data Sheet (1979).
Thorpe et al., 1987, Cancer Research 47:5924-5931.
Worrell et al., 1986, Anti-Cancer Drug Design 1:179-188.
Carlsson et al., 1978, Biochem. J. 173:723-737.
Jue et al., 1978, Biochemistry, 17:5399-5406.
Klotz and Heiney, 1962, Archives of Biochem. and Biophys. 96:605-612.
Yoshitake et al., 1979, Eur. J. Biochem. 101:395-399.
Hashida et al., 1984, J. Applied Bioch. 6:56-63.

Primary Examiner—Johann Richter
Attorney, Agent, or Firm—Albert P. Halluin

[57] ABSTRACT

This invention discloses heterobifunctional coupling agents for making a wide array of molecular conjugates. The agents contain a sterically hindered thiol, linked through a spacer arm to a second group reactive toward nucleophiles such as 1° and 2° amines or reactive thiols that are present on biological and organic materials. The coupling agents are useful for making conjugates containing a sterically hindered linkage.

9 Claims, 12 Drawing Sheets

AMINE-TO-THIOL COUPLING AGENTS

THIOL-TO-THIOL COUPLING AGENTS

COUPLING AGENTS AND STERICALLY HINDERED DISULFIDE LINKED CONJUGATES PREPARED THEREFROM

This application is a continuation of Ser. No. 07/206,573, filed Jun. 14, 1988 (now abandoned).

BACKGROUND OF THE INVENTION

1. Field of the Invention

This invention relates generally to the field of biochemistry and particularly to heterobifunctional coupling agents for making a wide array of molecular conjugates having numerous applications. More specifically, the agents contain a sterically hindered thiol, linked through a spacer arm to a second group reactive toward nucleophiles such as 1° and 2° amines or reactive thiols present on biological and organic materials. The coupling agents are useful for making conjugates containing a sterically hindered disulfide linkage, which conjugates are especially valuable for certain in vivo applications, such as targeted delivery of immunotoxins, drugs and radionuclides for cancer therapy and diagnosis.

2. Background Art

Conjugates between molecules with significantly different chemical or biological activities find broad use in analytical chemistry, clinical chemistry, and medicine. Enzymes directly or indirectly linked to antibodies find common use in immunoassays [Ishikawa et al. (1983) *Journal of Immunoassay* 4, 209-327]. Enzymes directly or indirectly linked to nucleic acid probes find increasing use in nucleic acid hybridization assays [Sheldon et al. [1987) *Clin. Chem.* 33, 1368-1371]. Conjugates between different antibodies may become therapeutically useful in antibody-dependent cell-mediated cytotoxicity [Titus et al. [1987) *J. Immunol.* 138, 4018-4022], a potential method for treating cancer, auto-immune disease, and immunological rejection reactions following tissue transplantation. The same therapeutic applications are envisioned for conjugates between toxins and antibodies, known as immunotoxins [Vitetta et al. (1987) *Science* 238, 1098-1104], as well as conjugates between antibodies and other therapeutic agents, including radionuclides and drugs of relatively low molecular weight. However, the total field of application of molecular conjugates is limited only by the imagination, as there are so many molecular functions, and within the functional domain of binding reactions, so many molecules with useful binding specificities (e.g., lectins for specific carbohydrates, hormones and cytokines for specific receptors, Staphylococcus protein A and certain complement components for immunoglobulins), that the total number of useful functional combinations is hard to count.

In some applications of molecular conjugates it is beneficial to use a crosslink between conjugated molecules which is cleavable under predictable or controlled conditions. In the field of pharmaceutical chemistry, it generally has been assumed that most effective immunotoxins require a cleavable bond between the toxin and the antibody which targets the toxin to a specific class of cells. Such immunotoxins are thought to operate by a multi-step pathway: binding to the cell surface, uptake into the interior of the cell, cleavage of the crosslink between antibody and toxin, and cell killing by the released toxin.

Three forms of chemical cleavability, generally applicable to molecular conjugation, have been engineered into immunotoxins. One uses an acid-labile crosslink, exploiting the fact that some of the intracellular compartments receiving internalized immunotoxins have pH values several pH units lower than that outside the cell. [Blatter et al. (1985) *Biochemistry* 24, 1517-1524]. A second cleavability tactic is to employ a peptide crosslinked with an amino acid sequence recognized by a specific protease [U.S. Pat. No. 4,571,958]. A third is the use of disulfide-containing crosslinks between antibody and toxin. The crosslinks may be cleaved rapidly upon addition of a relatively low (often approximately stoichiometric) concentration of a thiol. In as much as the thiol concentration in the extracellular fluid (e.g., blood plasma or lymph) is in the micromolar range, the intracellular thiol concentration exceeds 1 mM, largely due to the tripeptide, glutathione [Meister and Anderson (1983) *Annual Review of Biochemistry* 52, 711-760, see especially pp. 715-718]. Disulfide linked conjugates such as immunotoxins survive circulation in the blood well on the time scale of at least a few hours, yet are rapidly cleaved to release active toxin once they have been bound to and internalized by target cells.

U.S. Pat. No. 4,340,535 discloses such disulfide-crosslinked immunotoxins for the case in which the toxin is the ricin A chain and the antibody is either a whole immunoglobulin or an immunoglobulin fragment with binding specificity for an antigen carried by a cell. U.S. Pat. Nos. 4,350,626 and 4,450,154 claim immunotoxins in which a Fab [or Fab'] fragment of a tumor-specific antibody is coupled to the ricin A chain, with coupling occurring between cysteine-derived thiols on the two proteins, with or without an intervening bifunctional crosslinking group. U.S. Pat. Nos. 4,357,273 and 4,638,049 describe the analogous immunotoxins with diphtheria toxin being replaced by ricin A chain. U.S. Pat. No. 4,534,211 discloses conjugates where cytotoxic substances are attached to a cell-specific antibody or its fragment via at least one sulfur atom. The first of the above-named patents requires a disulfide bond within the crosslink. The last four allow such cleavable linkages to be made. None teaches how a sterically hindered disulfide bond might be made.

Recent pharmacokinetic studies of disulfide-linked immunotoxins show that they are less inert toward cleavage in the extracellular circulation than previously was thought [Blakey et al. (1987) *Cancer Research* 47, 947-952; Worrell et al. [1986) *Anti-Cancer Drug Design* 1, 179-188; Letvin et al. (1986) *J. Clin. Invest.* 77, 977-984]. Of the conjugate which has not been taken up from the blood by the various tissues, a significant fraction has been cleaved within eight hours of intravenous administration; essentially all has been split within 24 hours, long before the opportunity to kill target cells has been exhausted. This destructive side reaction may be the major limit to immunotoxin efficacy in vivo, because antibody cannot direct toxin to the target cells once the two molecules have separated. In addition, the antibody released from cleaved conjugate may compete with intact immunotoxin for cell surface binding sites. Accordingly, pharmaceutical science might be advanced greatly by the design of crosslinking agents with enhanced resistance to cleavage under extracellular conditions, which retain sufficient lability to break down on an effective time scale intracellularly.

Crosslinking of molecules, especially protein molecules, can be performed with homobifunctional or heterobifunctional reagents. The former require the molecules to be joined to have the same reactive groups. Because of this limitation homobifunctional reagents find little use in the modern art of macromolecular conjugation. Heterobifunctional crosslinking reagents require one of the molecules to be joined, hereafter called Partner B, to possess a reactive group not found on the other, hereafter called Partner A, or else require that one of the two functional groups be blocked or otherwise greatly reduced in reactivity while the other group is reacted with Partner A. In a typical two-step process for forming heteroconjugates, Partner A is reacted with the heterobifunctional reagent to form a derivatized Partner A molecule. If the unreacted functional group of the crosslinker is blocked, it is then deprotected. After deprotecting, Partner B is coupled to derivatized Partner A to form the conjugate. Primary amino groups on Partner A are reacted with an activated carboxylate or imidate group on the crosslinker in the derivatization step, and a reactive thiol or a blocked and activated thiol at the other end of the crosslinker is reacted with an electrophilic group or with a reactive thiol, respectively, on Partner B. When the crosslinker possesses a reactive thiol, the electrophile on Partner B preferably will be a blocked and activated thiol, a maleimide, or a halomethylene carbonyl (e.g., bromoacetyl or iodoacetyl) group. Because biological macromolecules do not naturally contain such electrophiles, they must be added to Partner B by a separate derivatization reaction. When the crosslinker possesses a blocked and activated thiol, the thiol on Partner B with which it reacts may be native to Partner B. Only when a thiol is reacted with a blocked and activated thiol can one be confident of forming a heteroconjugate with a cleavable disulfide linkage; which partner supplies which thiol species does not affect final conjugate structure.

Until recently, three heterobifunctional crosslinking agents were used almost to the complete exclusion of others in the preparation of disulfide-linked conjugates, including immunotoxins: N-succinimidyl-3-(2-pyridyldithio)propionate (SPDP) [Carlson et al. (1978) *Biochem. J.* 173, 727–737], 2-iminothiolane (IT) [Jue et al. (1978) *Biochemistry* 17, 5399–5406], and S-acetyl mercaptosuccinic anhydride (SAMSA) [Klotz and Heiney (1962) *Arch. Biochem. Biophys.* 96, 605–612]. All three react preferentially with primary amines (e.g., lysine side chains) to form an amide or amidine group which links a thiol to the derivatized molecule (e.g., a protein, such as an antibody) via a connecting short spacer arm, one to three carbon atoms long. The differences among these molecules illustrate the tactical choices in making disulfide-linked conjugates.

Molecules derivatized with SPDP possess a blocked and activated thiol, ready for attack by a thiol on another molecule to generate a disulfide-linked conjugate between the two molecules. Alternatively, treatment with a sufficient concentration of a low-molecular weight thiol such as 2-mercaptoethanol or dithiothreitol displaces the blocking group to leave a reactive thiol on the derivatized molecule, which can attack a blocked and activated thiol on another molecule to create a conjugate identical in structure to the one just described, above. Either way, the sulfur atom which SPDP contributes to the final disulfide linkage experiences minimal steric hinderance, being attached to a methylene group of a straight-chain spacer arm. Molecules derivatized with IT possess a reactive thiol, which either can react with a blocked and activated thiol on another molecule or can be blocked and activated itself, by reaction with a chromogenic aryldisulfide, such as 2,2'-dithiodipyridine, 4,4'-dithiodipyridine, or 5,5'-dithio-bis(2-nitrobenzoic acid). Other reagents for blocking thiols which may create various degrees of activation toward further thiol-disulfide exchange include alkyl alkonethiolsulfonates, alkoxycarbonylalkyl disulfides, and various sulfenyl chlorides [Smith et al. (1975) *Biochemistry* 14, 766–771, Carlsson et al., supra]. Here too, the sulfur atom which the crosslinker contributes to the final conjugate is attached to a methylene group of a straight-chain spacer arm. Molecules derivatized with SAMSA possess a blocked thiol which is not activated toward reaction with another thiol. The blocking acyl group must be displaced with a strong nucleophile, most commonly hydroxylamine, to release a reactive thiol, which then can be reacted as in the case of IT. However, this thiol is sterically more hindered than in the case of SPDP or IT, as either a carboxylate or a carboxymethyl group branches from the spacer arm at the carbon atom to which the thiol is attached (a position "alpha" to the thiol). The ambiguity with regard to the branching group derives from the asymmetry of SAMSA, which permits the nucleophilic amine to react with either a carbonyl group adjacent to the sulfur-bearing carbon atom or a carbonyl group one carbon atom further away. In addition, the SAMSA-originated thiol may be chemically activated or deactivated by the negative charge of the carboxylate or carboxymethyl branch; the exact nature of this neighboring-group effect probably will depend on the specific reaction involving the thiol.

Recently two novel families of crosslinking agents have been disclosed which contain blocked thiols and are singly branched alpha to the thiol in the manner of SAMSA, and which have been used to couple molecules via sterically hindered disulfide bonds. N-succinimidyl 3-(2-pyridyldithio)butyrate (SPDB) [Worrell et al., supra] is identical in structure to SPDP except that it contain a single methyl-group branch alpha to the sulfur atom which is blocked and activated by 2-thiopyridine. SMPT and SMBT [Thorpe et al. (1987) *Cancer Research* 47, 5924–5931] contain a phenylmethyl spacer arm between an N-hydroxysuccinimide-activated carboxyl group and the blocked thiol; both the thiol and a single methyl-group branch are attached to the aliphatic carbon of the spacer arm. The SMBT thiol is blocked by sulfite, to form a thiosulfate, which must be cleaved to release a reactive thiol before crosslinking can occur. The SMPT thiol is blocked and activated via a disulfide bond to 2-thiopyridine, in the manner of SPDP. Data of Thorpe et al. [supra] suggest that the benzene ring in the SMBT and SMPT spacer arm hinders thiol reactivity more than do the aliphatic straight-chain spacers of SPDP, IT, or SPDB, presumably because it creates branching beta to the thiol and possibly because of reduced flexibility. To date, SPDB and SMPT usage has been reported only in coupling reactions where the reagent-derivatized antibody is reacted with another molecule bearing a free thiol. Deblocking of the reagents for thiol attack on the activated thiol of another molecule appears not to have been done.

The important functional advantage of these novel disulfide-creating crosslinkers singly branched at the alpha carbon atom is that they result in less easily cleaved disulfide bonds than do unbranched crosslinkers; comparison of SAMSA in this regard has not been reported. This result has been seen in model thiol-disulfide exchange reactions in vitro and studies of immunotoxin survival in ciruclation in vivo [Worrell et al., supra; Thorpe et al., supra]. The increased resistance to cleavage in vivo is correlated with significantly prolonged blood clearance times, which should enhance immunotoxin delivery to target cells, particularly if the latter are part of a solid tumor. However, neither Worrell et al. [supra] or Thorpe et al. [supra] have sucessfully synthesized immunotoxin with disulfide crosslinks singly branded alpha to the thiol, that show improved tumor growth-suppression or erodiation.

The development of sterically hindered disulfide crosslinks such as molecules with two methyl groups attached to the thiol-bearing carbon atom of the spacer arm has, before the instant invention, been unsuccessful. Worrell et al. [supra] prepared 3-(2-pyridyldithio]isovaleric acid, a potential intermediate in the synthesis of a doubly branched analogue of SPDP, but were unable to convert it into a crosslinker by activating the carboxyl group with N-hydroxysuccinimide.

Worrell et al. [supra] compared the reactivity toward thioldisulfide exchange of the sterically hindered activated disulfide in this molcule to the reactivities of analogues which were singly branched and unbranched alpha to the activated thiol. A single alpha methyl group reduced reactivity by one order of magnitude; double branching reduced reactivity by three orders of magnitude. If a way could be found to incorporate such a hindered disulfide into a conjugate, the latter might have radically improved survival in vivo over the disulfide-linked conjugates with single branching which represent the current state of the art. However, the possibility also exists that such conjugates would be so inert toward thiol-disulfide exchange that they could no longer effectively kill target cells.

Before the present invention, sterically hindered disulfide crosslinkers having two methyl groups attached to the thiol-bearing carbon atom of the spacer arm, have not been synthesized; and there was no guarantee that if such compounds could be made, they would result in immunotoxins with improved therapeutic properties. The present invention discloses methods for synthesizing sterically hindered disulfide crosslinkers that are distinctly unique from that which is known. Immunotoxin conjugates made with these coupling agents have improved survival in vivo and increased tumoricidal activity.

SUMMARY OF THE INVENTION

The present invention overcomes the above described problems by providing a family of heterobifunctional coupling agents that when used according to the described methods, result in conjugates that have hindered disulfide linkages in which the thiol-bearing carbon atom of the coupling agent is attached to two methyl groups.

Using these coupling agents, 1° and 2° amine-containing materials can be conjugated to thiol-containing materials or thiol-containing materials can be conjugated to other thiol-containing materials. In addition, the coupling agent separating the conjugated materials can be varied as to divalent organic spacer content and length.

In one aspect, the invention provides reagents and methods for coupling 1° and 2° amine-containing materials with thiol-containing materials.

As a first embodiment of this aspect, coupling agents of the following general formula are described:

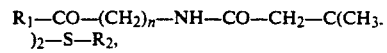

where
n is between 1 and 20,
$R_1$ is:

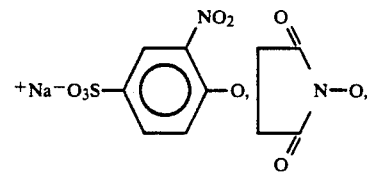

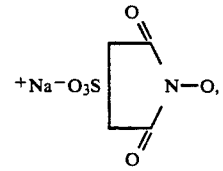

$R_2$ is:

—CO—CH$_3$, —CO—C$_2$H$_5$, or —CO—(CH$_2$)CH$_3$.

In a further embodiment, this aspect encompasses derivatives of 1° and 2°, amine-containing materials linked to the coupling agents to have the following formula:

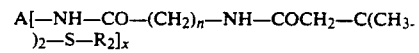

where A is a 1° or 2° amine-containing material attached to the coupling agent through the nitrogen atom of the amine, x is the number of amines on A that are derivatized, and $R_2$ is: —CO—CH$_3$, —CO—C$_2$H$_5$, or —CO—(CH$_2$)$_2$—CH$_3$.

In a third embodiment, this aspect encompasses conjugates and methods of producing such conjugate, that utilize the amine-to-thiol coupling agents and have the following formula:

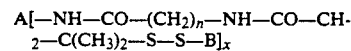

where A can be either a 1° or 2° amine-containing material linked to the coupling agent through the nitrogen atom of its amine, —CO—(CH$_2$)$_n$—NH—CO—C(CH$_3$)$_2$—S— is the coupling agent containing a hindered sulfur linked to a carbon atom attached to two methyl groups, B is a thiol-containing material linked to the hindered sulfur through a disulfide bond, n is 1 to 20, and x is the number of amines on A that are linked.

In another aspect, the invention provides reagents and methods for coupling thiol-containing materials with other thiol containing materials.

As a first embodiment of this second aspect, coupling agents of the following formula are described:

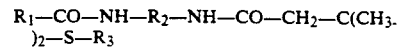

where $R_1$ is:

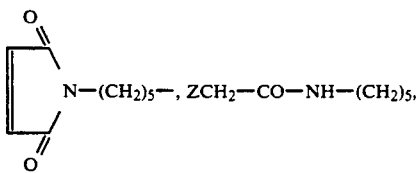

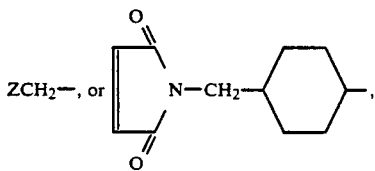

where
Z is Cl, Br, or I;
$R_2$ is:

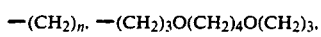

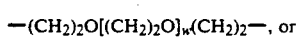

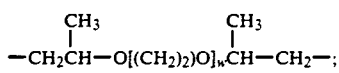

where
n is between 1 and 20, and
w is 1 to 100; and
$R_3$ is: $-CO-CH_3$, $-CO-C_2H_5$ or $-CO-(CH_2)_2-CH_3$.

In a further embodiment, this second aspect encompasses derivatives of thiol-containing material that are linked to the coupling agents to have the following formula:

$$A-[S-R'_1-CO-NH-R_2-NH-CO-CH_2C(CH_3)_2-S-R_3]_x$$

where A is the thiol-containing material covalently linked to the coupling agent through the sulfur atom of its thiol, x is the number of sulfur atoms on A that are linked;

$R'_1$ is:

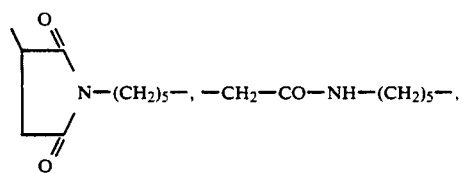

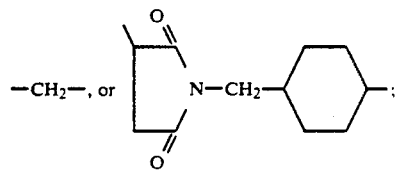

$R_2$ is:

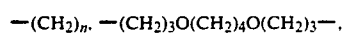

where
n is 1 to 20,
w is 1 to 100; and
$R_3$ is: $-CO-CH_3$, $-CO-C_2H_5$, $-CO-(CH_2)_2-CH_3$, or $-H$.

In a further embodiment, this aspect includes conjugates and methods for producing such conjugates that utilize the thiol-to-thiol coupling agents, which have the following formula:

$$A-[S-R'_1-CO-NH-R_2-NH-CO-CH_2-C(CH_3)_2-S-S-B]_x$$

where A is a thiol-containing material linked to the coupling agent through the sulfur atom of its thiol, x is the number of sulfur atoms on A that are linked through the coupling agent to B;

$R'_1$ is:

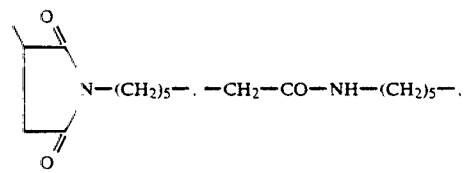

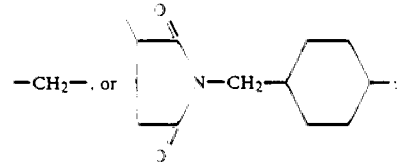

$R_2$ is:

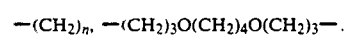

where
n is 1 to 20,
w is 1 to 100; and,
B is the same or a different thiol-containing material.

In a third aspect, the invention describes methods of synthesizing amine-to-thiol coupling agents of the formula:

$$R_1-CO-(CH_2)_n-NH-CO-CH_2-C(CH_3)_2-S-CO-R_2$$

wherein
$R_1$ is

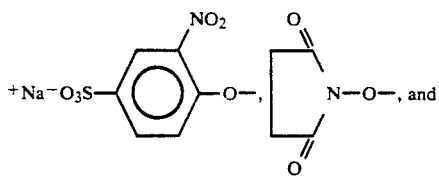

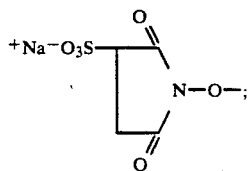

$R_2$ is an alkyl or aryl group, and, h is between 1 and about 20 comprising the steps;
(a) reacting in a solvent containing an acid neutralizing compound, a dimethylacryloyl halide of the formula

W—CO—CH=C(CH₃)₂ where W is chloride or bromide, with a short chain alkyl ester of an aminoalkylenecarboxylic acid of the formula

Y—O—CO—(CH₂)ₙ—NH₂ .

wherein Y is selected from the group consisting of (CH₃)₃C—, H₃C—, and H₅C₂—, to form a product of the formula

Y—O—CO—(CH₂)ₙ—NH—CO—CH=C(CH₃)₂;

(b) reacting the product of step (a) with a thiol acid of the formula H—S—CO—R₂ where R₂ is defined above, using a Michael-type reaction, to form a product of the formula

Y—O—CO—(CH₂)ₙ—NH—CO—CH₂—C(CH₃)₂—S—CO—R₂;

(c) reacting the product of step (b) with an acid to form a product of the formula

HOOC—(CH₂)ₙ—NH—CO—CH₂—C(CH₃)₂—S—CO—R₂;

(d) reacting in a solvent, in the presence of a carbodiimide, the product of step (c) with sodium [4-hydroxy-3-nitro]benzene sulfonate (HNSA) to form a product of the formula

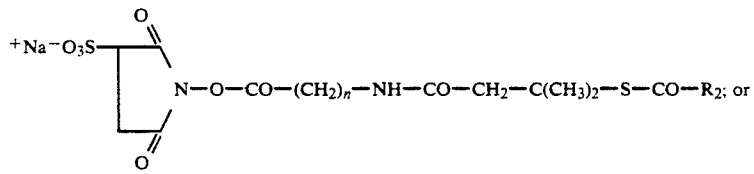

(e) reacting in a solvent, in the presence of a carbodiimide, the product of step (c) with sulfo-N-hydroxysuccinimide to form a product of the formula

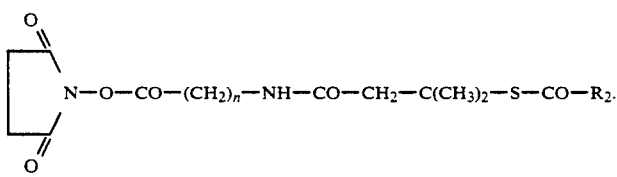

(f) reacting in a solvent, in the presence of a carbodiimide, the product of (c) with N-hydroxysuccinimide to form a product of the formula

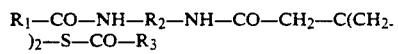

In a fourth aspect, the invention describes methods of synthesizing thiol-to-thiol coupling agents of the formula:

R₁—CO—NH—R₂—NH—CO—CH₂—C(CH₂)₂—S—CO—R₃ wherein R₁ is selected from the group consisting of

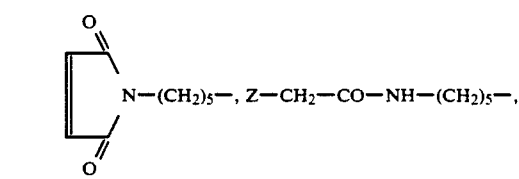

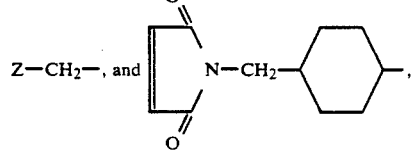

wherein

Z is a halogen selected from the group consisting of Cl, Br, and I;

$R_2$ is an acyclic aliphatic spacer arm selected from the group consisting of $-(CH_2)_n-$, $-(CH_2)_3O(CH_2)_4O(CH_2)_3-$, $-(CH_2)_2O[(CH_2)_2O]_w(CH_2)_2-$, and $-CH_2-\overset{CH_3}{\underset{|}{CH}}O[(CH_2)_2)O]-\overset{CH_3}{\underset{|}{CH}}-CH_2-$, where
n is between 1 and about 20,
w is between about 1 and about 100; and,
$R_3$ is an alkyl or aryl group comprising the steps;

(a) reacting in a solvent containing an acid neutralizing compound a dimethylacryloyl halide of the formula

W—CO—CH=C(CH$_3$)$_2$ where W is chloride or bromide, with either a 1-t-butoxycarbonylalkanediamine or a 1-t-butoxycarbonylalkyloxydiamine of the formula (CH$_3$)$_3$C—O—CO—NH—R$_2$—NH$_2$ where R$_2$ is defined above, to form a product of the formula (CH$_3$)$_3$C—O—CO—NH—R$_2$—NH—CO—CH=C(CH$_3$)$_2$;

(b) reacting the product of (a) with a thiol acid of the formula

H—S—CO—R$_3$ where R$_3$ is defined above, using a Michael-type reaction, to form a product of the formula (CH$_3$)$_3$C—O—CO—NH—R$_2$—NH—CO—CH$_2$—C(CH$_3$)$_2$—S—CO—R$_3$;

(c) reacting the product of step (b) with an acid to form a product of the formula

NH$_2$—R$_2$—NH—CO—CH$_2$—C(CH$_3$)$_2$—S—CO—R$_3$;

(d) reacting in a solvent, the product of step (c) with 6-maleimido-hexanoic acid-sodium (4-hydroxy-3-nitro-) benzene sulfonate to form a product of the formula

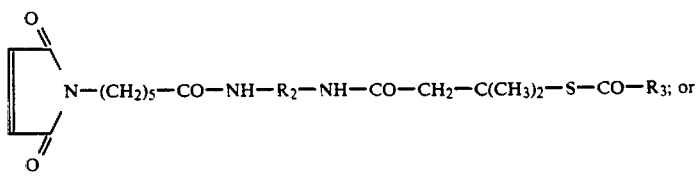

(e) reacting in a solvent the product of step (c) with succinimidyl (4-(N-maleimidomethyl) cyclohexane-1-carboxylate to form a product of the formula

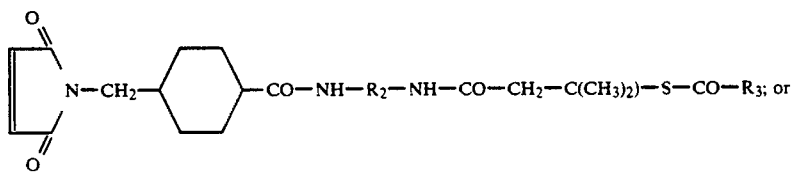

(f) reacting in a solvent the product of (c) with a compound of the formula

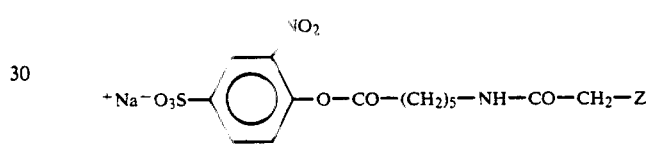

where Z is defined above, to form a product of the formula

Z—CH$_2$—CO—NH—(CH$_2$)$_5$—CO—NH—R$_2$—NH—CO—CH$_2$—C(CH$_3$)$_2$—S—CO—R$_3$;

(g) reacting in a solvent the product of (c) with a compound of the formula

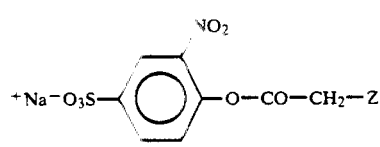

where Z is defined above, to form a product of the formula

Z—CH$_2$—CO—NH—R$_2$—NH—CO—CH$_2$—C(CH$_3$)$_2$—S—CO—R$_3$.

In a fifth aspect, the invention describes methods for killing human cancer cells with a cytocidally effective amount of a conjugate of a toxin and an anti-tumor antibody, wherein the hindered disulfide coupling agents are utilized.

BRIEF DESCRIPTION OF THE DRAWINGS

FIG. 9 is a graphic illustration showing the pharmacokinetic parameters in Craig Dawley rats of 260F9-PL-rRTA, 260F9-IT-rRTA, and 260F9-SMCC-rRTA.

DETAILED DESCRIPTION OF THE PREFERRED EMBODIMENTS

A. Definitions

Figure 1:
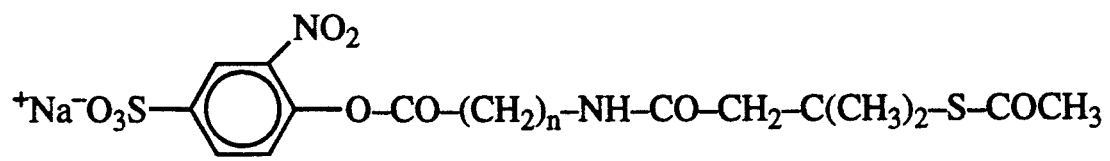
FIG. 1 shows the chemical formulas of the amine-to-thiol coupling agents.
Figure 1:
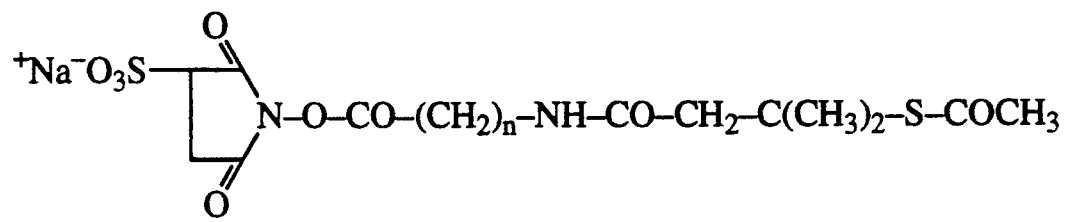
Figure 1:
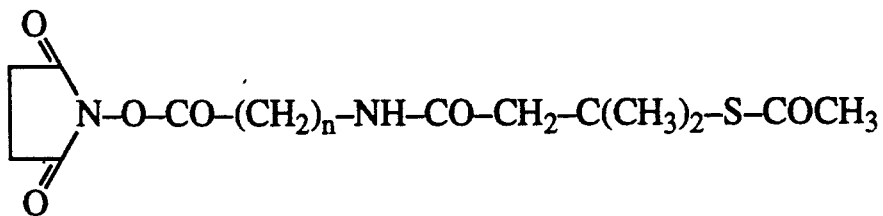

As used herein, the following terms have the following meanings:

"Amine-containing material" refers to compounds other than amino acids that contain primary (1°) and secondary (2°) amines that are free to react with the coupling agent(s) of this invention to form an amide linkage. Such materials include not only the naturally occurring materials but also the recombinant, mutationally or chemically modified equivalents. Most preferred are primary amine-containing materials, as for example proteins or peptides that contain lysine amino acids wherein a primary amine is located at the ε position on its aliphatic chain. Examples of such materials include antibodies or antibody fragments, carrier proteins such as bovine serum albumin, key-hole limpet hemocyanin (KLH), ovalbumin, enzymes, toxins, hormones, growth factors, amine-containing lipid vesicles, polypeptides, cells, virus particles, chromatographic matrices, lymphokines and cytokines as exemplified in the definition of thiol-containing materials, polyamines, including 2° amine-containing polymers such as poly(ethyleneimine), poly(vinylamine), and the like, aminated chromatographic supports such as aminated sepharose, aminated silica gel, and the like, and amine-containing membranes such as aminated nylon or aminated plastics such as poly(styrene).

The amine-containing material is preferably a protein, peptide or polypeptide that contains a primary amine, more preferably one that specifically binds to a cell, more preferably an antibody or an antibody fragment, and most preferably an anti-tumor monoclonal antibody (one that recognizes human cancer cells) such as those directed against breast and/or ovarian cancer. It should be noted that a material can be a naturally occurring material or can be of synthetic origin, as desired, e.g., poly(lysine) or synthetic polypeptides, or the like.

"Thiol-containing material" refers to compounds other than amino acids that contain thiols which are free to react with the conjugating compounds herein to form a disulfide or thioether linkage. Such materials includeg not only the naturally occurring material but also the recombinant mutationally or chemically modified equivalents. Examples are, ricin toxin A or B chain, diphtheria toxin A or B chain, Fab' fragments, toxin, cytokines with thiol groups not necessary for their biological activity, such as, for example, interleukin-2, colony stimulating factors (CSFs), such as M-CSF, GM-CSF, and G-CSF, interleukin-1, interleukin-3, interleukin-4, interfrons (IFNs) such as IFN-α, IFN-β, and IFN-γ, as well as other therapeutically important proteins such as tissue plasminogen activator. Also included as thiol-containing materials are insoluble matrices such as chromatographic materials, derivatized polysaccharides, silica gel derivatives, and the like, which contain a thiol group. In addition, the term includes inert materials such as polystyrene beads that have been derivatized to contain the thiol groups. Enzymatically active toxins of bacterial, fungal, or plant origin, or fragments of such toxins are preferred and are exemplified by diphtheria A chain, exotoxin A chain (from *Pseudomonas aeruginosa*), ricin toxin A chain, abrin A chain, modeccin A chain, alpha-sarcin, *Aleurites fordii* proteins, dianthin proteins, *Phytolacca americana* proteins (PAPI, PAPII, and PAP-S), momordica charantia inhibitor, curcin, crotin, saponaria officinalis inhibitor, gelonin, mitogellin, restrictocin, phenomycin, and enomycin. More preferred are ricin toxin A chain, non-binding active fragments of diphtheria toxin, abrin A chain, PAPII, and Fab' fragments. Most preferred are ricin toxin A chain and Fab' fragments.

"Ricin toxin A chain" refers to a protein whose amino acid sequence is substantially similar to that of the ricin A peptide of ricin toxin that is extractable from castor bean seeds. The ricin A of castor beans is approximately 265 amino acids in length and has a molecular weight of approximately 32,000 daltons. However, it is known that the precise sequence varies depending on the variety of bean, and indeed, that at least two slightly different forms of ricin A may be present in a single variety.

The ricin toxin A chain may be obtained from natural sources or by recombinant means. For example one method of obtaining, the ricin subunit A from native sources may be obtained by extraction and purification of ricin from the seeds of *Ricinus communis* and separation of subunit A from ricin, according to the method of S. Olsnes and A. Pihl, *Biochemistry*, 12:3121-3126 (1973). The subunit A solution thus obtained contains 2-mercaptoethanol (ME) and is, therefore, immediately prior to its use, subjected to Sephadex G25 column chromatography equilibrated with 5 mM acetate buffer-0.14M sodium chloride-1 mM ethylenediaminetetracetic acid (EDTA) (pH 5.5) to remove ME. SDS-PAGE can be used to detect if any subunit B or intact ricin is present.

Alternatively, the ricin subunit A may be obtained by recombinant means, as, for example, by the method disclosed in U.S. Pat. No. 4,689,401, issued Aug. 25, 1987, the disclosure of which is incorporated herein by reference.

"F(ab)' fragments" as used herein refers to the F(ab)' regions or fragments of the immunoglobulin molecule. These regions may be generated by enzymatic digestion of the antibody such as pepsin digestion followed by reductive cleavage of the fragment so produced. Digestion may take place under any conditions known to those skilled in the art. One suggested condition is to obtain a solution of purified IgG in 0.1M acetate buffer (pH 4.5) and react it with pepsin at 37° C. for about 18 hours. The digestion product is then subjected to Sephadex G200 column chromatography in saline to remove protein eluted at the molecular weight associated with the particular fragment desired. Purity and identiy of the fragment can be determined, e.g., by means of electrophoresis with SDS-PAGE. After reduction, the product may be subjected to Sephadex G25 column chromatography equilibrated with 5 mM acetate buffer—0.14M sodium chloride—1 mM EDTA (ph 5.5) to remove the reducing agent (e.g., 2-mercaptoethanol) to give the Fab' fragment with a thiol.

The types of antibodies that may be employed include immunoglobulins obtained by immunizing a mammal with an appropriate antigen under conditions well known in the art, or monoclonal antibodies, typically obtained by means of hybridoma technology, also well known in the art (see, e.g., Taylor-Papadimitrou et al., *Int. J. Cancer* (1981) 28:17-21 and Yuan et al., JNCI (1982) 68:719-728.

"activated ester leaving moiety" refers the OR portion of an ester (COOR) that is a leaving group in the reaction between the ester and a primary or secondary amine to form an amide linkage. Examples of such leaving groups include:

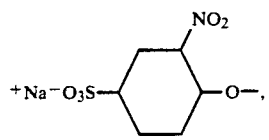

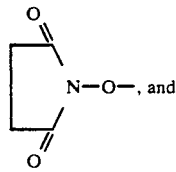

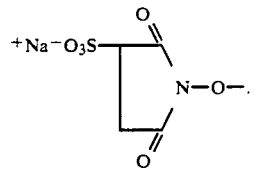

"thiol blocking moiety" refers to compounds that covalently bind the sulfur atom of a thiol, thus preventing the thiols nucleophilic and reductive reactivity. Examples of such thiol blocking moieties include —CO—$CH_3$, —CH—$C_2H_5$ and —CO—$(CH_2)_2$—$CH_3$.

"thiol alkylating moiety" refers to alkylating compounds that can react with the sulfur atom of a thiol to form a new carbon sulfur bond thereby creating a thioether linkage. Examples of such compounds are:

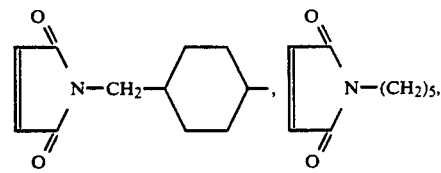

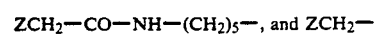

where Z is Cl, Br or I.

"thiol group(s) has been activated" refers to reaction of the sulfur atom of a thiol-containing material with an electrophilic aromatic disulfide, as for example: 5,5'-dithiobis(2-nitro-benzoic acid) (DTNB), 2,2'-dithiodipyridine (2,2'DTDP), and 4,4'-dithiodipyridine (4,4'DTDP).

"Michael-type reaction" refers to a nucleophilic addition of a nucleophile to a substrate of the form —C=C—Z, where Z is CHO, COR, COOR, $CONH_2$, CN, $NO_2$, etc., with the nucleophile bonding to the carbon away from the Z group. For example, the addition of the nucleophilic sulfur atom of a thiol acid, H—S—CO—R, where R is —$CH_3$, —$C_2H_5$ or —$(CH_2)_2$—$CH_3$, to the substrate —CH=C$(CH_3)_2$ will give the product

—$CH_2$—C$(CH_3)_2$—S—CO—R.

"1-t-butoxycarbonylalkanediamine" refers to an alkane containing butoxycarbonyldiamine where alkane is a divalent covalent organic spacer moiety, —$(CH_2)_n$—, with n being between 1 and 20, inclusive.

"1-t-butoxycarbonylalkoxydiamine" refers to an alkloxy containing butoxycarbonyldiamine where alkloxy or divalent covalent organic spacer moieties exemplified by: —$(CH_2)_3O(CH_4O(CH_2)_3$— (4,9 dioxadodecane); —$(CH_2)_2O[(CH_2)_2O]_w(CH_2)_2$; (derived from polyethylene glycol); or

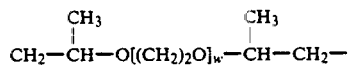

derived from Jeffamine ® ED, Texaco Chemical Co.), where w is an integer between 1 and 100.

Divalent covalent organic spacer moieties are selected to provide separation between the thiol or amine reactive group at one end of the coupling agent and the thiol reactive group at the other end of the coupling agent. It is common to observe that close proximity between the coupled moieties (for example an antibody and a toxin protein) is deleterious and that increased separation is advantageous.

In selecting spacer moieties it is generally desirable to avoid groups which will interact significantly in a physical, chemical or immunological sense with the moieties present within the environment of use. Typically, since the coupling agent is usually used in an aqueous medium, the spacer units should not react with the aqueous medium and should not be unduly hydrophobic. If the spacer has substantial hydrophobic regions, they may bind to hydrophobic regions of the materials being coupled and coprecipitate.

With these general considerations in mind, acyclic aliphatic compounds are most prefered as spacer moieties. Typical acyclic aliphatic spacers can be branced or straight chain. They can contain from 1 to about 20 chain carbons. Preferred acyclic aliphatic spacers contain from about 2 to about 8 carbon atoms in the spacer chain and are saturated. Examples of acyclic aliphatic spacers include ethylene, propylene, butylene, 2,4-dimethylbutylene, pentylene, 2-methylpentylene, n-hexylene, decylene and the like.

Another group of useful spacers include oxygen-containing divalent units. The oxygens can be present as ether oxygens. Ethers tend to decrease hydrophobicity and increase the hydrophilic character of the spacer. They are also advantageous for the very practical reason that a number of such materials are available commercially.

Representative oxygen-containing spacers include the poly(ethylene glycol) ether and the poly(oxyalkyleneamine)s such as the JEFFAMINES.

"Cytocidally effective amount" refers to an amount of the conjugate effective to kill the human cancer cells in question.

The thiol-containing materials can be linked to either the same or different materials containing thiols or amines via the coupling agents herein to form crosslinked proteins or peptides, immunotoxins, labeled antibodies, immobilized insoluble antibodies, or chromatographic absorbents.

The compounds used for coupling agents herein are typically initially reacted with the appropriate functional group of the amine or thiol-containing material and subsequently with the thiol functionality of thiol-containing material to form a disulfide bond.

B. Modes for Carrying Out the Invention

1. Compounds Useful As Conjugating Agents

Two types of compounds are useful for coupling the materials described herein. One is useful for coupling amine-containing materials to thiol-containing materials, and the other is useful for coupling together thiol-containing materials.

The amine-to-thiol coupling agents have the formula:

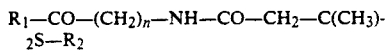

wherein
n is an integer from 1 to about 20,
$R_1$ is:

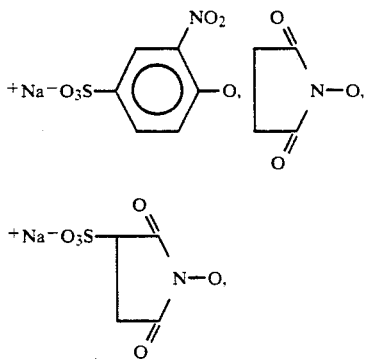

or any other active ester that has a good activated ester leaving group; and
$R_2$ is: $-CO-CH_3$, $-CO-C_2H_5$, $-CO-(CH_2)_2CH_3$, or any other thiol blocking group.

The amine-to-thiol coupling agents can be synthesized by first reacting in a solvent containing an acid neutralizing compound, a dimethylacryloyl halide of the formula, $W-CO-CH=C(CH_3)_2$, with a short chain alkyl ester of an aminoalkenecarboxy of the formula,

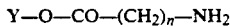

to form a product of the formula,

The reaction is best done at room temperature with a solvent that solubilizes the two reactants and is inert towards the reaction. Favored solvents are exemplified by methylene chloride, ether, chloroform, benzene, tetrahydrofuran, dioxane and hexane. Methylene chloride is the most preferred. In addition, an acid neutralizing compound, capable of neutralizing the production of HCl generated during the course of the reaction, is included. The most effective acid neutralizing compounds are tertiary amines, such as triethylamine, as well as pyridine. In addition, the halide of the dimethylacrylocyl halide (W) can be either chloride or bromide with chloride being the most preferred.

A variety of short chain alkyl groups (Y) can be linked with the ester of the amino alkylenecarboxylic acid. Effective groups are methyl and ethyl with tert-butyl being the most preferred. The number of alkene groups (n) can be anywhere from 1 to 20 with 2 being the most preferred. A most preferred short chain alkyl ester of the aminoalkylenecarboxylic acid is t-butyl-$\beta$-alanine hydrochloride, $((CH_3)_3C-O-CO(CH_2)_2-NH_2)$.

The first reaction step results in a product having at one end a carboxylic acid protected from nucleophilic attack of the next reaction step by a bulky short chain alkyl group (Y) with the tert-butyl group being favored. The products other end acts as a good substrate for nucleophilic addition of a thiol acids nuceleophilic sulfur atom in a Michael-type reaction.

The Michael-type reaction of the first-reaction product with a thiol acid such as thiol acetic acid ($H-S-CO-CH_3$) adds a sulfur atom to the dimethyl carbon to produce a second-reaction product with a hindered thiol linked to a thiol blocking moiety, having the formula,

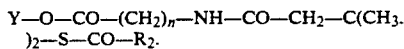

The thiol blocking moiety, $R_2$, can be varied depending on the type of thiol acid used in the Michael-type reaction. For example, thiolacetic acid results in an effective thiol blocking moiety of $-CH_3$.

The carboxylic acid ether is next reacted with a suitable acid to remove the short chain alkyl group (Y) to produce the corresponding carboxylic acid product,

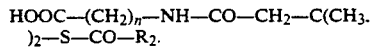

The acid used will depend on the short chain alkyl group. If a tert-butyl group is protecting, trifluoroacetic acid is preferred. If a methyl or ethyl group is protecting, aqueous HCl or aqueous $H_2SO_4$ is preferred.

The carboxylic acid product can be purified by any number of methods known in the art, as for example, with thin layer chromatography and recrystallization from $CHCl_3$- hexane. The purified carboxylic acid product is ready to be made into any of the above described amine-reactive esters.

To synthesize the amine-to-thiol coupling agent where $R_1$ is

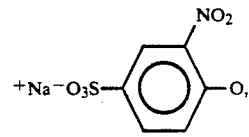

the purified carboxylic acid product is reacted with sodium [4-hydroxy-3-nitro]benzene sulfonate (HNSA) in the presence of a carbodiimide such as diisopropylcarbodiimide or more preferably dicyclohexylcarbodiimide in a suitable solvent such as dimethylsulfoxide or more preferably dimethylformamide. The reaction mixture is stirred overnight at room temperature, diisopropylurea or dicyclohexylurea, depending on the carbodiimide used, precipitates and is filtered off, and the product

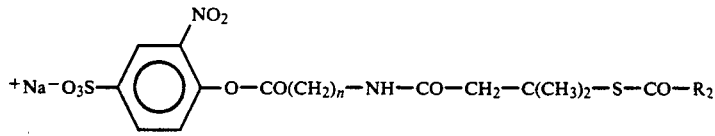

precipitates when diethylether is added.

To synthesize the amine-to-thiol coupling agent where $R_1$ is

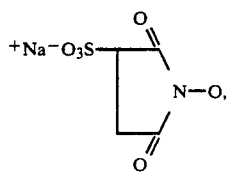

the purified carboxylic acid product is reacted with sulfo-N-hydroxy-succinimide (sulfo-NHS) under the same reaction conditions as called for to produce the HNSA active ester described above, to product the compound,

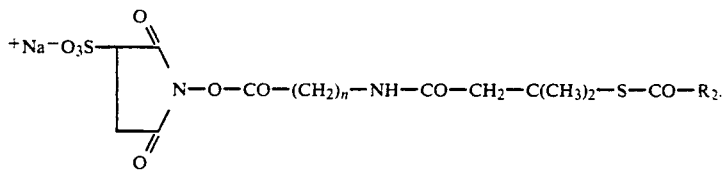

To synthesize the amine to thiol coupling agent where $R_1$ is

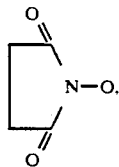

the purified carboxylic acid product is reacted with N-hydroxysuccinimide in the presence of the carbodiimide described above in a suitable solvent such as dimethylformamide, dimethylsulfoxide, methylene chloride or more preferably chloroform. Again, the reaction mixture is stirred overnight at room temperature to form a precipitate which is filtered off with the addition of diethylether precipitating the desired product of the formula

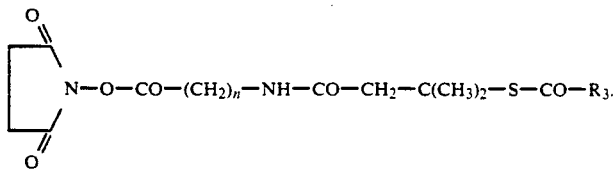

The second coupling agent herein crosslinks two thiol-containing materials, and is of the formula:

$$R_1\text{—CO—NH—}R_2\text{—NH—CO—CH}_2\text{C(CH}_3)_2\text{—S—}R_3$$

wherein $R_1$ is a thiol reactive moiety, as for example;

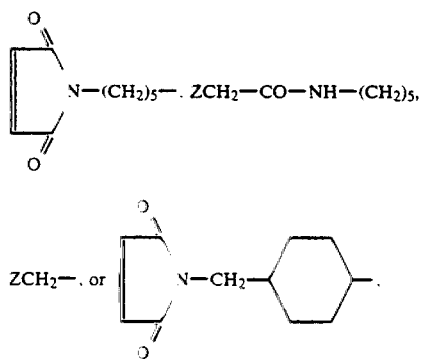

where
Z is Cl, Br, or I, preferably Br,
$R_2$ is:

$-(CH_2)_n$, $-(CH_2)_3O(CH_2)_4O(CH_2)_3-$, $-(CH_2)_2O[(CH_2)_2O]_w(CH_2)_2-$, or

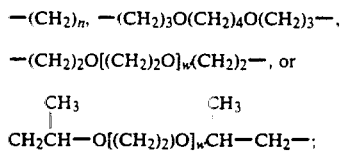

where
n is between 1 and 20,
w is 1 to 100; and
$R_3$ is: $-CO-CH_3$, $-CO-C_2H_5$ or $-CO-(CH_2)_2-CH_3$ and any other effective thiol blocking moiety, preferably $-CO-CH_3$.

The thiol-to-thiol coupling agents can be synthesized by first reacting in a solvent containing an acid neutralizing compound a dimethylacryloyl halide of the formula, W—CO—CH=C(CH₃)₂, with either a 1-t-butoxycarbonylalkanediamine or a 1-t-butoxycarbonylalkyloxydiamine of the formula, (CH₃)₃C—O—CO—NH—R₂—NH₂

(where $R_2$ is defined above with —(CH₂)₃O(CH₂)₄O(CH₂)₃— being most preferred) to form a product of the formula, (CH₃)₃C—O—CO—NH—R₂—NH—CO—CH=C(CH₃)₂.

The reaction is best done at room temperature with a solvent that solubilizes the two reactants and is inert towards the reaction. Favored solvents are exemplified by ehter, chloroform, benzene, tetrahydrofuran, dioxane, hexane with methylene chloride being most preferred. In addition, an acid neutralizing compound, capable of neutralizing the production of HCl generated during the course of the reaction, is included. The most effective acid neutralizing compounds are tertiary amines such as triethylamine, as well as pyridine. In addition, the halide of the dimethylacryloyl halide (W) can be either chloride or bromide with chloride bing most preferred.

The first reaction step results in a product having at one end a nitrogen protected by a t-butoxycarbonyl group (BOC). The BOC group is important because it allows nucleophilic addition to be done selectively to the other end of the molecule which acts as a good substrate for nucelophilic addition of a thiol acids nucleophilic sulfur atom in a Michael-type reaction.

The Michael-type reaction of the first reaction product with a thiol acid such as thiolacetic acid (H—S—CO—CH₃) adds a sulfur atom to the dimethyl carbon to produce a second reaction product with a hindered thiol linked to a thiol blocking moiety having the following formula, (CH₃)₃C—O—CO—NH—R₂—NH—CO—CH₂—C(CH₃)₂S—CO—R₃.

The thiol blocking moiety, $R_3$, can be varied depending on the type of thiol acid used in the Michael-type reaction. For example, thiolacetic acid results in an effective thiol blocking moiety of —CH₃.

The BOC protecting group is next removed "de BOCed" by reacting the third reaction product with an acid such as formic acid or more preferably trifluoroacetic acid to produce a compound of the formula,

NH₂—R₂—NH—CO—CH₂—C(CH₃)—S—CO—R₃.

This compound can be reacted with one of four reagents to obtain a specified thiol reactive moiety, $R_1$.

To synthesize the thiol-to-thiol coupling agent where $R_1$ is

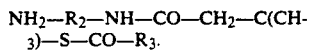

the fourth reaction product is reacted with N-maleimido-6-aminocaproic HNSA ester in the presence of a solvent such as methylene chloride, dimethylformamide, dimethylsulfoxide or more preferably chloroform to produce.

N—(CH₂)₅—CO—NH—R₂—NH—CO—CH₂—C(CH₃)₂—S—CO—CH₃.

To synthsize the thiol-to-thiol coupling agent where $R_1$ is

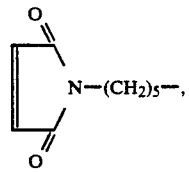

the fourth reaction product is reacted with succinimidyl-4-(N-maleimidomethyl)-cyclohexane-1-carboxylate (SMCC) in the presence of a solvent such as dimethylsulfoxide or more preferably, dimethylformamide, to produce, N—CH₂—⟨cyclohexane⟩—CO—NH—R₂—NH—CO—CH₂—C(CH₃)₂—S—CO—CH₃.

To synthesize the thiol-to-thiol coupling agent where $R_1$ is Z—CH₂—CO—NH—(CH₂)₅—, the fourth reaction product is reacted with the 1-hydroxy-2-nitro-4-benzene sulfonic (HNSA) active ester of acetyl halide amide of 6-amino caproic acid, in a solvent such as dimethyl sulfoxide or more preferably dimethylformamide, to produce,

Z—CH₂—CO—NH—(CH₂)₅—CO—NH—R₂—NH—CO—CH₂—C(CH₃)₂—S—CO—CH₃.

To synthesize the thiol-to-thiol coupling agent where $R_1$ is $Z$—$CH_2$—, the fourth reaction product is reacted with the HNSA active ester of acetyl halide, in a solvent such as dimethyl sulfoxide or more preferably dimethylformamide, to produce,

Z—CH$_2$—CO—NH—R$_2$NH—CO—CH$_2$—C(CH$_3$)$_2$—S—CO—CH$_3$.

Another route for synthesizing this second type of compound is to react a compound of the formula: BOCHN—CH(COOH)C(CH$_3$)$_2$—S—S—C(CH$_3$)$_2$—CH(COOH)NHBOC (where BOC is a t-butoxycarbonyl group) with a reducing agent such as dithiothreitol or 2-mercaptoethanol followed by reaction with an acetylating agent such as acetic anhydride to produce the compound

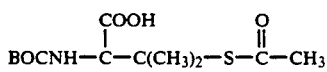

This compound is then reacted with trifluoroacetic acid to remove the protecting BOC group. Thereafter, the resulting amine is reacted with one of the four reagents described above to produce one of the four compounds.

Derivatization and Conjugation

In accordance with the invention herein, amine-containing materials can be conjugated to thiol-containing materials, or thiol-containing materials can be coupled to each other or to other thiol-containing materials. The choice of coupling agent will depend, in part, on what materials are to be coupled.

A. Amine-Containing Materials to Thiol-Containing Materials

Typically in such a conjugation, the amine-containing material is first derivatized with the coupling agent, and the product is then reacted with the thiol-containing material, which has had its thiol activated by reaction with a compound that will form a mixed aryl-alkyl disulfide. Examples of such compounds include 5,5'-dithiobis(2-nitrobenzoic acid) (DTNB), 2,2'-dipyridyl disulfide, 4,4'-dipyridyl disulfide, etc. Preferably, 5,5'-dithiobis(2-nitrobenzoic acid) is employed.

In this preferred procedure, the amine-containing material, such as an antibody, is derivatized with one of the coupling compounds:

R$_1$—CO—(CH$_2$)$_n$—NH—CO—CH$_2$C(CH$_3$)$_2$—S—R$_2$, where n is 1 to about 20;

R$_1$ is an activated ester leaving group such as,

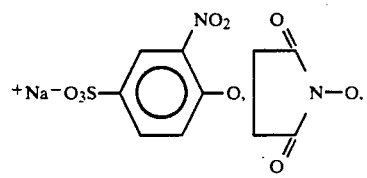

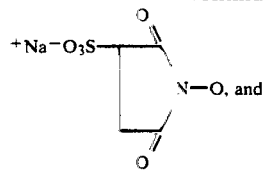

R$_2$ is a thiol blocking moiety such as,

—CO—CH$_3$, CO—C$_2$H$_5$, or —CO—(CH$_2$)$_2$CH$_3$.

The result is an amine-containing material derivative to the formula:

A[—NH—CO—(CH$_2$)$_n$—NH—CO—CH$_2$—C(CH$_3$)$_2$—S—R$_2$]$_x$ where A is a 1° or 2° amine-containing material attached to the coupling agent through the nitrogen atom of the amine, and x is the number of amines on A that are derivatized. The value of x depends on, e.g., reaction conditions and the particular biological material, but is preferably 1–5, most preferably 1.

The reaction may take place generally using >1:1 molar amount of coupling compound to amine-containing material, at temperatures ranging generally from about 0° to 40° C., depending on the reagent employed. Temperatures of about 0° to 40° C. may be preferred for reagents containing N-hydroxysuccinimide, or sulfo-N-hyroxysuccinimide. The reaction is carried out for a time sufficient for completion, depending, e.g., on the types of reagents and the temperature. Generally, the reaction takes place for at least 5 hours, preferably 5 to 20 hours. If the derivative terminates with S—COCH$_3$, the derivatized material is then reacted with hydroxylamine at pH 8.0 to liberate a free thiol (it is deacetylated) to yield the intermediate, A[—NH—CO—(CH$_2$)$_n$—NH—CO—CH$_2$—C(CH$_3$)$_2$—S—H]$_x$. This reaction preferably is carried out at ambient conditions (e.g., room temperature) for as long as needed, preferably about one hour.

After the optional desalting step, the number of thiols on the material is quantitated. This may be done by titrating the material with 5,5-dithiobis-(2-nitrobenzoic acid) and determining how much thio-(2-nitrobenzoic acid) is released. A procedure of which is common in the art.

Once the number of thiols is determined, the derivatized material is reacted with a thiol-containing material, the thiols of which have been activated by reaction with compounds as described above such as DTNB. The activation reaction may be carried out as follows, giving as an example, ricin toxin A chain: After the ricin subunit A is properly prepared (e.g., for recombinant ricin A, reduced with a reducing agent such as dithiothreitol (DTT) and dialyzed against phosphate buffer), the ricin toxin chain is reacted with a molar excess (preferably 2-4 fold) of the activating reagent and the number of activated groups per ricin toxin A is determined. The activated ricin toxin A is then concentrated and desalted prior to reaction with the derivatized amine-containing material.

The reaction between the two materials typically takes place at from 0° to 30° C., more preferably at room temperature. Reaction time varies with temperatures, but may range generally from about 5 to 48 hours, more preferably 10 to 30 hours. The molar ratio of thiol-containing material to derivatized amine-containing material may range from about 1 to 3 moles of thiol-containing material per mole of thiol of the derivatized amine-containing material, more preferably 1.5-2 moles.

After the reaction, the conjugated protein may be purified by a means as by high pressure liquid chromatography or molecular sieve Sephadex chromatography, etc. Fractions having the correct conjugate molecular weight can be determined by, e.g., SDS-PAGE gel electrophoresis; pooled and concentrated.

B. Thiol-Containing Materials to Thiol-Containing Materials

Typically in such a conjugation, a first thiol-containing material, as for example, Fab' fragment, is reacted with the coupling compound:

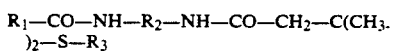

wherein $R_1$ is a thiol reactive moiety, as for example;

Z is Cl, Br, or I, preferably Br;

$R_2$ is: $-(CH_2)_n-$, $-(CH_2)_3O(CH_2)_4O(CH_2)_3-$, $-(CH_2)_2O[(CH_2)_2O]_w(CH_2)_2$, or

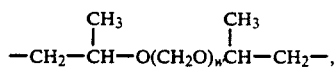

where n is 1 to 20, and w is 1 to 100, and $R_3$ is: $-CO-CH_3$, $-CO-CH_2H_5$, $-CO-(CH_2)_2-CH_3$ and any other effective thiol blocking moiety, preferably $-CO-CH_3$. The result is a derivative having the formula:

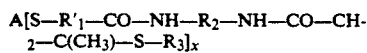

wherein $R'_1$ is the reacted-thiol alkylating moiety linked through a thioether bond to the first thiol-containing material (A), $R_2$ and $R_3$ are as defined immediately above, and x is the number of reacted thiols on A.

Derivatives corresponding to the coupling agents above have the following formula:

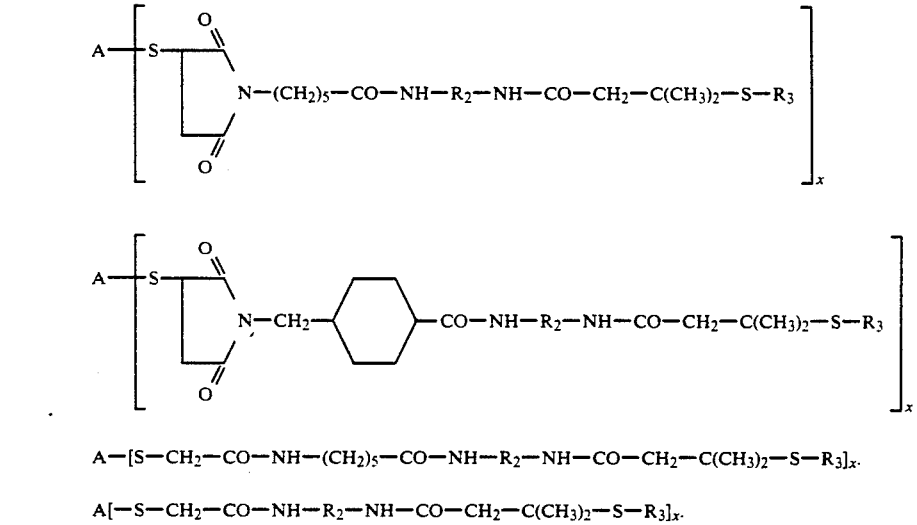

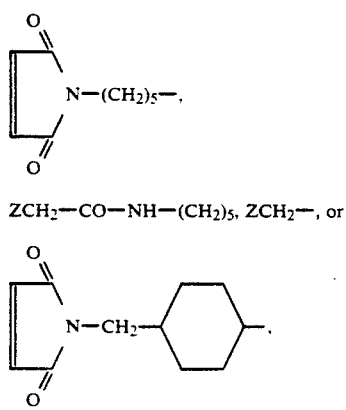

where

Reaction conditions will be approximately stoichiometric to 3-fold molar excess of coupling reagent, generally 0°–30° C., preferably ambient conditions, until complete reaction occurs, generally 1–30 hours.

The derivative can have its thiol blocking group removed by reaction with hydroxylamine, as described above. Once this is done, the derivative is reacted with a second, identical or different thiol-containing material (HS-B) that has had its thiols activated as described above, with, for example, DTNB. The reaction is favored most when the steoichiometry is between 1–3 mole excess of the activated second-thiol-containing material over the derivative. The reaction conditions will be the same or similar to those described above (0°–30° C., preferably ambient temperature, for 1–30 hours).

The resulting conjugates of two thiol-containing materials have the following formula and are derived from the corresponding derivatives above:

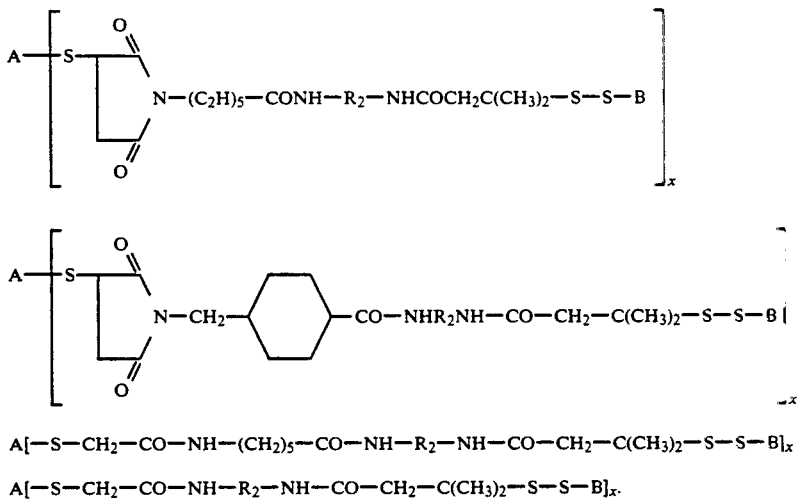

A[—S—CH₂—CO—NH—(CH₂)₅—CO—NH—R₂—NH—CO—CH₂—C(CH₃)₂—S—S—B]ₓ

A[—S—CH₂—CO—NH—R₂—NH—CO—CH₂—C(CH₃)₂—S—S—B]ₓ.

The results of these experiments is a family of conjugates That contain hindered disulfide crosslinks that have two methyl groups attached to the thiol-bearing carbon atom, with the following general formula:

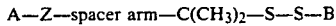

A—Z—spacer arm—C(CH₃)₂—S—S—B wherein A-Z is a thiol-containing or amine-containing material attached to the sulfur atom of the thiol group or to the nitrogen atom of the amine group thereof, S-B is a thiol-containing material, attached to the sulfur atom of the thiol thereof, and Z is NH or S arising from the linked amine or thiol, whichever is the case, of A. The —C(CH₃)₂—S—S— moiety represents the hindered disulfide bond arising from the conjugation of the thiol of the material, represented by S-B, to the thiol of the coupling agent. The spacer arm moiety varies in its acyclic aliphatic carbon content depending on the coupling agent employed.

The resulting conjugate may be purified by any suitable technique known to those skilled in the art. If the conjugate is a toxin conjugate such as ricin toxin A chain to antibody, a preferred purification procedure is described in copending U.S. application Ser. No. 917,469 filed Oct. 10, 1986, the disclosure of which is incorporated herein by reference.

Briefly, the toxin conjugates are purified by providing a conjugation mixture containing toxin conjugate, unconjugated selective binding molecule, and unconjugated toxin protein, removing the unconjugated toxin protein from the mixture on a sizing column, and removing the unconjugated binding molecule from toxin conjugate loaded on a hydrophobic gel with an eluting solution comprising an aqueous salt solution.

The resulting conjugate, particularly that wherein an antibody is conjugated to ricin toxin A chain, has decreased in vivo lability and increased efficacy over the same conjugate except having a non-hindered disulfide linkage. Preferably, the conjugates are immunotoxins useful for in vivo anti-tumor therapy. They may also be conjugated lymphokines such as IL-2 or IFN-β conjugated to an antibody or fragment thereof useful for anti-tumor, anti-inefective, or immunomodulating therapy. In addition, the compounds may be useful for in vivo diagnostic monitoring of drug therapy, for example, an antibody conjugated to a label moiety.

In the examples that follow, further illustrations of the invention are presented. These examples are not intended to limit the invention to their particular illustrations. In the examples, all temperatures are in degrees Celsius unless otherwise noted.

EXAMPLE I

Amine-to-Thiol Coupling Agent Synthesis

Figure 2A:
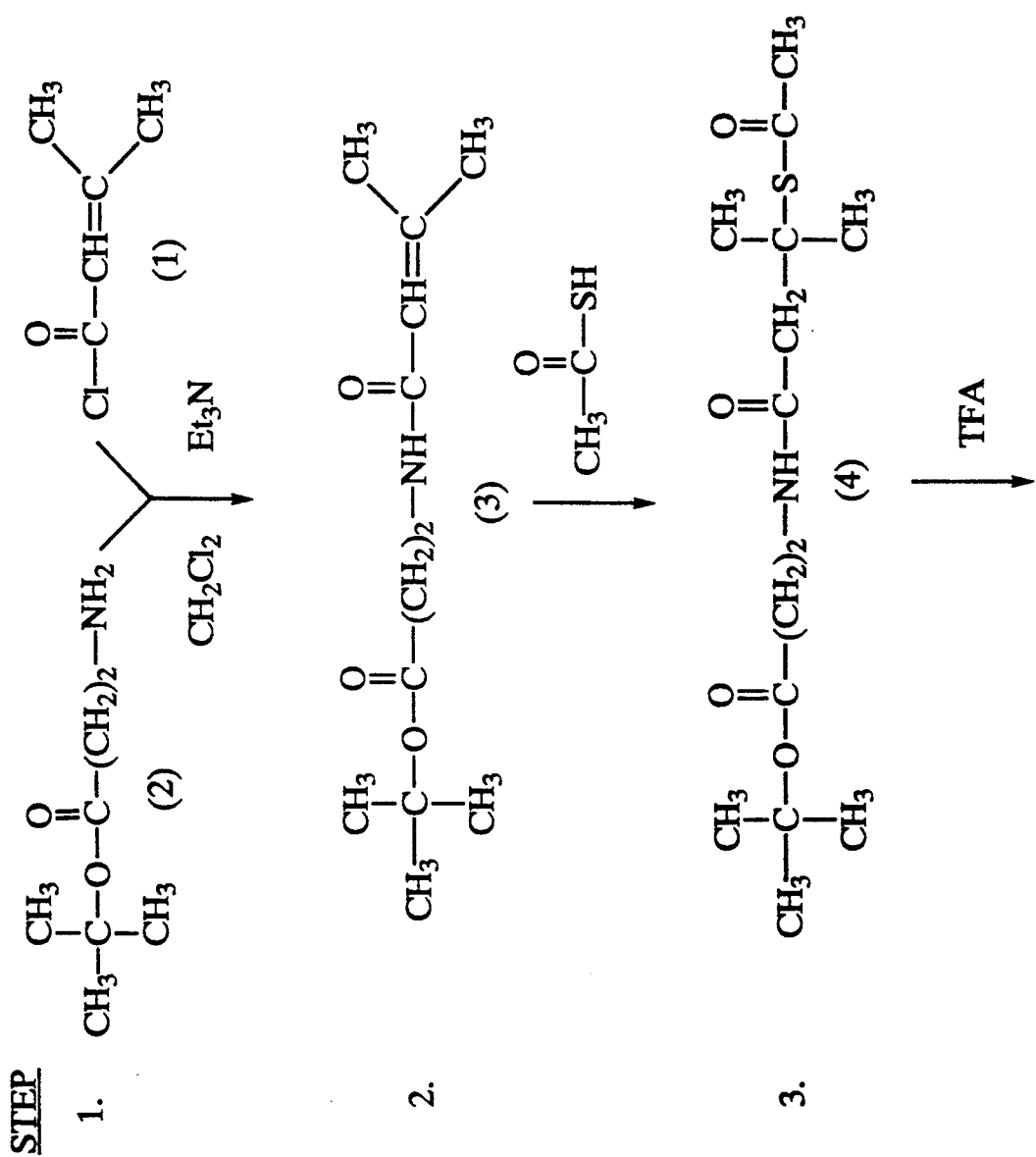
FIG. 2 shows the reaction scheme of synthesizing the HNSA-ester, the NHS-ester and the sulfo-NHS-ester of the amine-to-thiol coupling agents shown in FIG. 1.
Figure 2B:
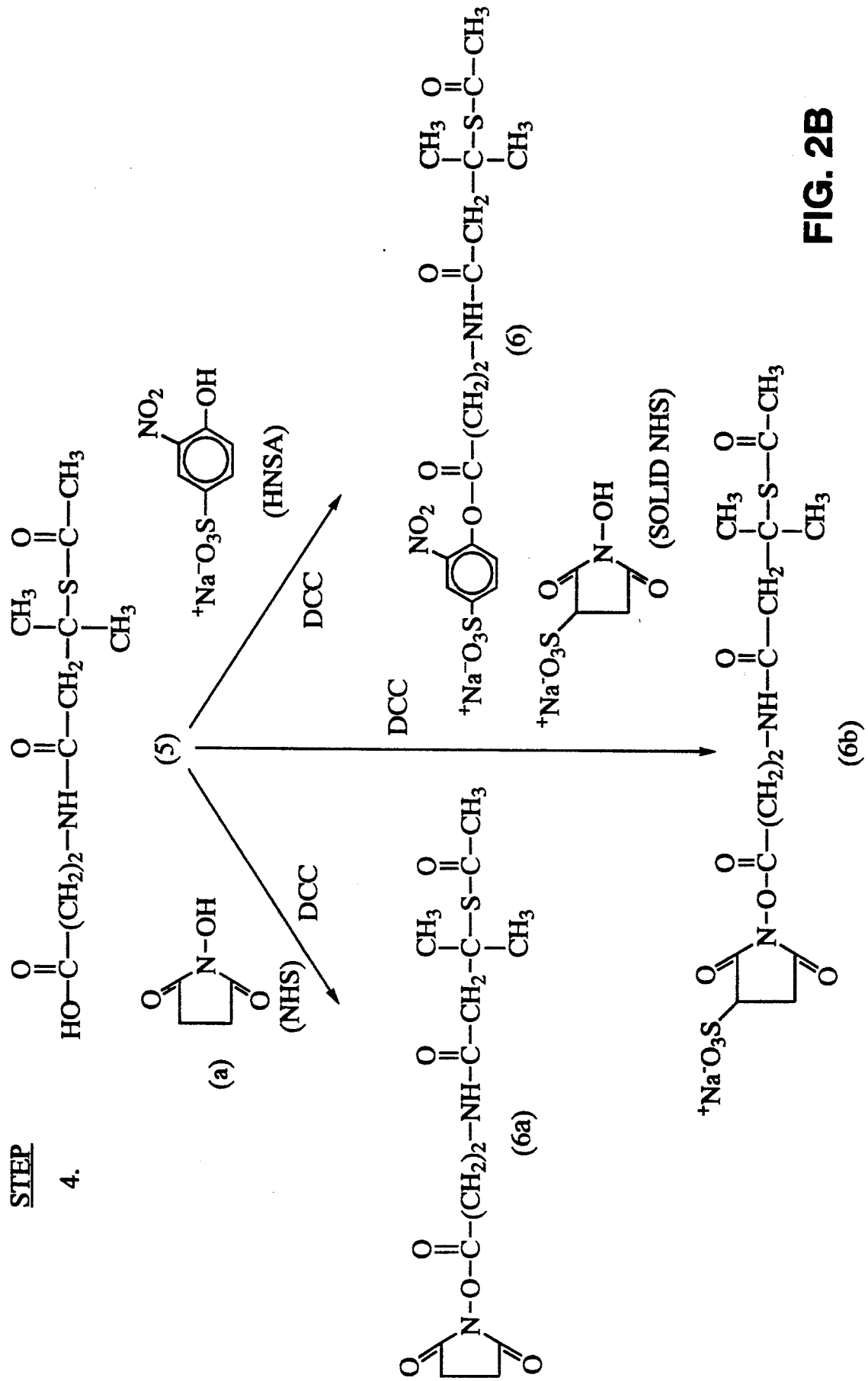
Figure 3:
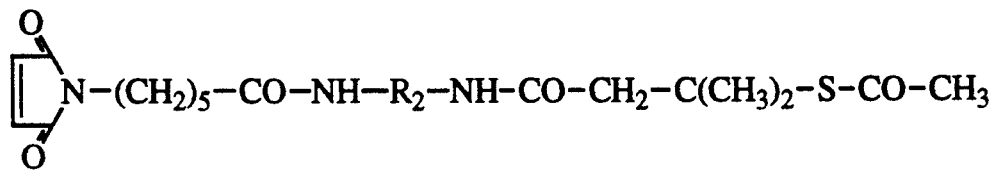
FIG. 3 shows the chemical formulas of the thiol-to-thiol coupling agents.
Figure 3:
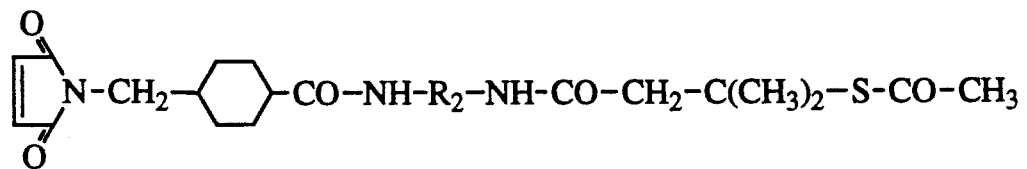
Figure 3:
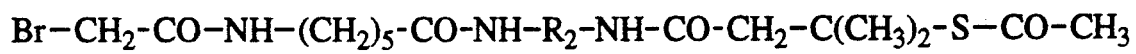
Figure 3:

The synthesis of 3-acetylthio-3-methylbutyl-β-alanine and its HNSA and NHS active ester is shown in FIG. 2, to which the parenthetical numerals given below refer.

Step 1:

Dimethylacryloylchloride (2) (1.1 ml, 10 mmole) was dissolved in 10 ml CH₂Cl₂ under N₂ in a 100-ml, 3-neck round-bottom flask fitted with a dropping funnel. t-Butyl-β-alanine hydrochloride (1) (1.82 g, 10 mmole) was dissolved in 10 ml Cu₂Cl₂ in a 25 ml Erlenmeyer flask and one equivalent of triethylamine (1.4 ml) was added. The precipitate that formed was filtered off and washed with 3 ml CH₂Cl₂. The resulting solution of t-butyl-β-alanine plus the wash was placed in the dropping funnel. Triethylamine (1.4 ml) was added to the solution in the funnel, which solution was then added dropwise to the dimethyl acryloyl chloride solution.

When addition was complete the funnel was rinsed with 10 ml CH₂Cl₂. The mixture was stirred at room temperature (RT) for two hours. At this time thin layer chromatography on silica gel plates (5% methanol in CHCl₃) indicated no dimethyl acrylic acid and the presence of a new spot corresponding to the product, t-butyl-β-alanyldimethyl acrylate (3). The reaction mixture was diluted to about 50 ml with CH₂Cl₂, washed with H₂O (15 ml×2), and saturated aqueous NaCl, and dried over MgSO₄. Evaporation of the solvent gave a pale yellow oil (1.64 g). This crude product (3) was purified in 2 batches on a 4 mm Chromatotron plate. The chromatography was started in 0.5% methanol in CHCl₃ until the fast-moving band was off. The product was eluted with 2% methanol in CHCl₃. Yield was 1.5 g, 66% of theoretical recovery.

Step 2:

To 2.47 g (10.9 mmole) t-butyl-β-alanyldimethyl acrylate in a 50-ml, round-bottom flask was added 10 ml of freshly double-distilled thiolacetic acid. The flask was flushed with N₂ and fitted with a condenser and Y tube for N₂ purge. The reaction mixture was refluxed under N₂ for four hours. The solution was cooled and diluted with about 75 ml ethyl ether. The ether solution was washed with 5% acetic acid, H₂O (×2), and saturated aqueous NaCl, then dried over MgSO₄. Evaporation of the ether gave a colorless oil.

Step 3:

The crude product (4) was treated with 15 ml trifluoroacetic acid (TFA) and stirred at RT for one hour. Then the TFA was evaporated to give a very pale yellow oil. This crude product was purified in two batches on a 4 mm chromatotron plate, starting with CHCl₃ to remove a fast running component, and eluting the product (5) with 5% methanol in CHCl₃. The product crystallized upon evaporation of the solvent. The product was recrystallized from CHCl₃-hexane, giving 1.40 g (5.67 mmole), 52% of theoretical recovery.

Step 4:

The HNSA ester of 3-acetylthio-3-methylbutyryl-β-alanine (6) was made as follows: the product of step 3 (5), 617 mg (2.5 mmole), was weighed into a 10 ml round-bottom flask. Sodium [4-hydroxy, 3-nitro-]benzene sulfonate (HNSA), 602 mg (2.5 mmole), was dissolved in ~2.5 ml dimethyl formamide (DMF) and added to the flask. Dicyclohexylcarbodiimide (DCC) 515 mg (2.5 mmole), was added. The mixture was stirred (protected from moisture by a drying tube) overnight at room temperature. Precipitated dicyclohexylurea was filtered off and washed with ~0.5 ml DMF. The filtered solution was added dropwise to 50 ml stirred ether. After stirring about ½ hour and letting settle for 15 minutes, the ether was decanted. Fresh ether was added and the stirring, settling, and decanting steps were repeated for a total of four times. The precipitate was originally very gummy, and became a pale yellow solid. It was filtered and dried. The final yield of HNSA ester protected linker (PL) was 535 mg, 46% of theoretical recovery.

Step 4a:

The N-hydroxysuccinimide ester was also prepared, as follows: To 0.494 g (2 mmole) of the product of step 3 (5) in a 25-ml, round-bottom flask was added 0.23 g (2 mmole) N-hydroxysuccinimide (NHS) in ~7 ml CH₂Cl₂, and 0.412 g of DCC was added. The reaction was stirred overnight at RT. The precipitated dicyclohexyl urea was filtered off and washed with CH₂Cl₂. Evaporation of the methylene chloride gave a white powder, which was recrystallized from ethanol. Yield was 0.35 g, 50% of theoretical recovery.

Step 4b:

The sulfo-N-hydroxysuccinimide ester of 3-acetylthio-3-methylbutyryl-β-alanine (6b) is made as follows: The product of step 3(5), 617 mg (2.5 mmole), was weighed into a 10 ml round-bottom flask. Sulfo-N-hydroxysuccinimide (sulfo-NHS), 542 mg (2.5 mmole), is dissolved in ~2.5 ml DMF and added to the flask. Dicyclohexylcarbodiimide (DCC), 515 mg (2.5 mmole), is added. The mixture is stirred (protected from moisture by a drying tube) overnight at room temperature. Precipitated dicyclohexylurea is filtered off and was washed with ~0.5 ml DMF. The filtered solution is next added dropwise to 50 ml stirred ether. After stirring about ½ hour and letting settle for 15 minutes, the ether is decanted. Fresh ether is added and the stirring, settling, and decanting steps are repeated for a total of four times. The precipitate is filtered and dried. The theoretical yield is 1.59 g.

EXAMPLE II

Thiol-to-Thiol Coupling Agent Synthesis

Figure 4:
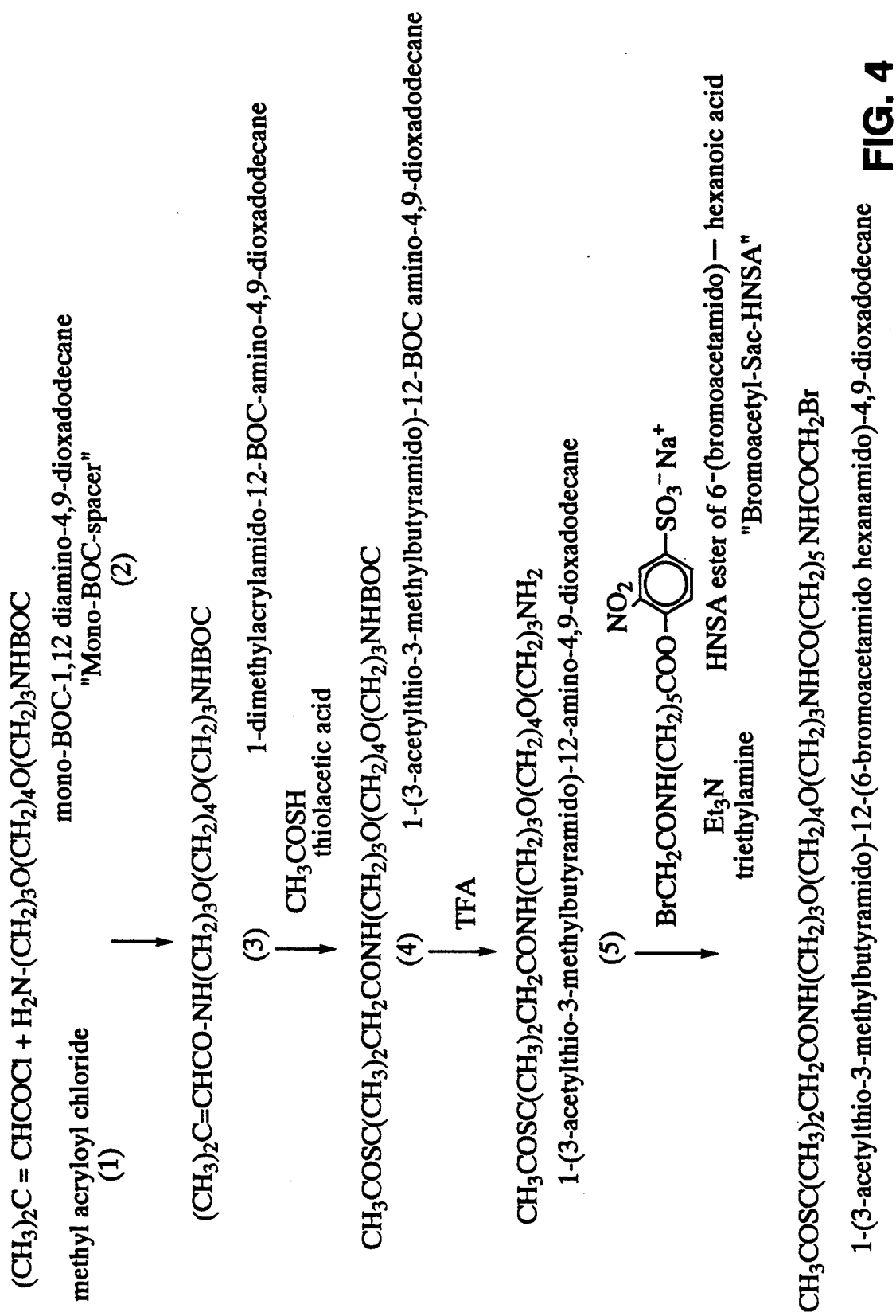
FIG. 4 shows the reaction scheme of synthesizing a thiol-to-thiol coupling agent shown in FIG. 3.

The synthesis of 1-(3-acetylthio-3-methylbutyramido)-12-(G-bromoacetamidohexanamido)4,9-dioxadodecane is shown in FIG. 4, to which the parenthetical numerals given below refer.

Dimethyl acryloyl chloride (1) (0.6 g, 5 mmole) was dissolved in 5 ml methylene chloride in a 50 ml three-neck round bottom flask fitted with a nitrogen inlet and outlet and a dropping funnel. "Mono-BOC-spacer" (2) (1.52 g, 5 mmole) was dissolved in 5 ml methylene chloride and placed in the dropping funnel. The solution of mono-BOC-spacer was added dropwise to the stirred solution of dimethyl acryloyl chloride at room temperature. This was followed by 0.7 ml triethylamine (5 mmole). The reaction mixture was stirred overnight at room temperature. The solution was diluted to 50 ml with methylene chloride, washed with water (10 ml×2) and saturated sodium chloride solution, and dried over magnesium sulfate. Evaporation of the solvent gave a pale yellow oil which was purified by Chromatotron chromatography using 2% methanol in chloroform. Yield=0.64 g (1.7 mmole) (33%) of 1-dimethylacrylamido-12-BOC-amino-4,9-dioxadodecane (3).

To 1-dimethylacrylamido-12-BOC-amino-4,9-dioxadodecane (0.6 g, 1.6 mmole) in a 25 ml round bottom flask was added 10 ml of freshly distilled thiolacetic acid. The solution was stirred and refluxed under nitrogen for four hours. The solution was cooled and diluted to 70 ml with diethyl ether. The ether solution was washed with water, 5% acetic acid, water, and saturated sodium chloride solution, and dried over magnesium sulfate. Concentration gave a pale brown oil: 1-(3-acetylthio-3-methylbutyramido)-12-BOC-amino-4,9-dioxadodecane (4). This crude product was stirred with 5 ml trifluoroacetic acid for ½ hour at room temperature. The TFA was removed by evaporation with a stream of nitrogen. Yield (crude product)=0.59 g (1.6 mmole, ~100%) of 1-(3-acetylthio-3-methyl-butyramido-12-amino-4,9-dioxadodecane (5).

The crude 1-(3-acetylthio-3-methylbutyramido)-12-amino-4,9-dioxadodecane (200 mg, 0.53 mmole) was dissolved in 2 ml dimethylformamide and bromoacetyl-Sac-HNSA (280 mg, 0.4 mmole) was added. Triethylamine was added until the mixture measured pH 7.5 using damp pH paper. The solution was stirred overnight at room temperature, then diluted with 40 ml diethyl ether. The ether solution was washed with water, dried over magnesium sulfate, and evaporated. Yield of crude product=220 mg (0.36 mmole) (68%) 1-(3-acetylthio-3-methylbutyramido)-12-(6-bromoacetamidohexanamido)4,9-dioxadodecane (6).

EXAMPLE III

Conjugation of Monoclonal Antibody to Recombinant Ricin Toxin A (rRTA)

DNA constructs and transformed microorganisms used to synthesize soluble, intracellularly produced recombinant RTA (rRTA) are described in U.S. Pat. No. 4,689,401 issued Aug. 25, 1987, the disclosure of which is incorporated herein by reference.

The rRTA (150 mg, 10 mg/ml) was reduced with 1 mM DTT at 23° C. for 60 minutes. The reduced rRTA was dialyzed against 100 mM sodium phosphate pH 8, 1 mM EDTA, 30% glycerol (NaP). The thiols of the freshly reduced rRTA were activated by reaction at 23°

C. for 60 minutes with a 5-fold molar excess of DTNB at a protein concentration of 10 mg/ml in NaP. The number of TNB groups per rRTA was determined to be 0.95.

The activated rRTA was concentrated using an Amicon Centricon 30 concentrator and desalted over a PD10 sizing column equilibrated with NaP, giving a rRTA concentration of 5–10 mg/ml.

A breast tumor specific monoclonal antibody (260F9; produced from the cell line deposited as ATCC No. 8488), was prepared as described in copending U.S. Ser. No. 842,476 filed Mar. 21, 1986. the disclosure of which is incorporated herein by reference. A total of 166 mg of the antibody (9 mg/ml) was derivatized with a 14 molar excess of HNSA protected ester linker (PL):

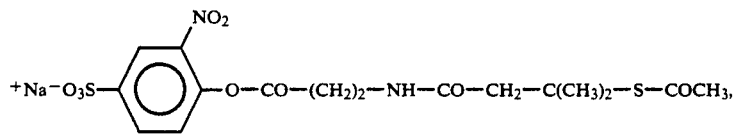

in 100 mM Hepes, 0.2 m NaCl, 1 mM EDTA, pH7.6 at RT for 14 hours. The derivatized protein was then deacetylated with 50 mM hydroxylamine by reaction at RT for one hour. After the reaction mixture was desalted over a PD10 column equilibrated with NaP, the number of thiol groups per antibody was quantitated to be 1.6 using a sample of the mixture in the DTNB assay, described above.

The derivatized antibody and activated rRTA were reacted together for 72 hours using a 1.5 molar excess of rRTA over titrated thiols of the antibody (157 mg Mab, 105 mg rRTA).

The conjugated protein (260F9-PL-rRTA) was purified by column chromatography. Ten ml fractions were collected and 10 μl were analyzed on a stacked non-reducing SDS-PAGE gel having a 6%/15% stack. Fractions having conjugate were pooled and concentrated using an Amicon Centricon 30 membrane. The conjugate was stored at a concentration of 1–2 mg/ml at 4° C.

EXAMPLE IV

In Vitro Cytotoxicity Testing of Immunoconjugate

In vitro cytotoxicity was tested using a 24 hour protein synthesis assay as well as a three day MTT assay which measures the cellular levels of mitochondrial reductase, [Green, L. M. et al. (1984) *J. Immunol. Meth.* 70:257–268]. The disclosure of which is incorporated by reference. 260F9-PL-rRTA was analysed and compared to that of a conjugate of the same antibody and rRTA but having a 2-iminothiolane (IT) linker, not protected with two methyl groups at the alpha-carbon (260F9-IT-rRTA). Production of conjugates using 2-iminothiolane is disclosed in commonly owned, copending U.S. patent application Ser. No. 842,476 filed Mar. 21, 1986, the disclosure of which is incorporated herein by reference. Briefly, DTNB was reacted with antibody at RT for 15 minutes in a phosphate-EDTA buffer and chilled to 0° C. Enough 2-iminothiolane was added to give 2.5 IT molecules/antibody molecule. Then freshly reduced RTA was dialyzed against phosphate-EDTA buffer and added to the derivatized antibody to give 1.0–1.2 free thiols on RTA/blocked thiol on derivatized antibody. This mixture was reacted at RT for two hours and then purified by column chromatography, dialyzed, and rechromatographed to isolate and purify the resulting immunotoxin.

24 Hour Protein Synthesis Assay

The two conjugates cytotoxicity were compared using cell lines; OVCAR3 from a human ovarian carcinoma and MCF-7 from a human breast carcinoma. The assay was performed by adding forty-thousand test cells (in 1 ml medium) to each of 8 glass vials. Next, serial dilution of conjugate (in PBS + 100 ug/ml bovine serum albumin) was added to the vials. After incubation at 37° C. for 22 hours, the medium was aspirated, the monolayers were washed with phosphate buffered saline (PBS), and methionine-free medium supplemented with $^{35}S$ methionine. The vials were further incubated for two hours at 37° C., the medium was removed, and the cells were washed twice with 2 ml of 10% trichloroacetic acid containing 1 mg/ml methionine. The cells were dried, scintillation fluid was added, and the radioactivity was counted in a scintillation counter. Cytotoxicity was expressed as the tissue culture inhibitory dose of conjugate that resulted in 50% of control (untreated) protein synthesis (TCID 50%), as determined by $^{35}S$ methionine uptake.

The results of these cytotoxicity tests, reported in Table 1, indicate the conjugate to be of similiar toxicity as the iminothiolane based conjugate.

TABLE 1

| Conjugate | $TCID_{50}$ (nM) | |
|---|---|---|
| | OVCAR-3 | MCF-7 |
| 260F9-IT-rRTA | 0.114 | 0.013 |
| 260F9-PL-rRTA | 0.288 | 0.019 nM |

72 Hour MTT Assay

Inhibition of mitochondrial reductase and as well as specificity of 260F9-PL-rRTA was tested and compared to that of a similar PL-rRTA conjugate linked to a mouse myeloma antibody (MOPC21) which shows no known reactivity (MOPC21-PL-rRTA). The cytotoxicity of the two conjugates towards a human breast cell line, MX-1, and a human fibroblast, HS27-F, were compared. The assay was performed by incubating the test cells with varying dilutions of conjugates for 72 hours, at which time the dye 3-(4,5-dimethylthiazol-2-yl)-2, 5-diphenylformazan (MTT) is added to determine the level of mitochondrial reductase activity remaining.

The results shown in Table 2 indicates effective and specific toxicity of 260F9-PL-rRTA toward the beast carcinoma cell line as compared to the fibroblast cell line. The non-reactive conjugate is greater than 1800 fold less toxic than 260F9-PL-rRTA for the breast carcinoma cell line and virtually non-toxic towards the fibroblast cell line.

TABLE 2

| Conjugate | $TCID_{50}$ (nM) | |
|---|---|---|
| | MX-1 | HS27F |
| 260F9-PL-rRTA | 0.0425 | >107.2 |

TABLE 2-continued

| Conjugate | TCID$_{50}$ (nM) | |
|---|---|---|
| | MX-1 | HS27F |
| MOPC21-PL-rRTA | 78.29 | >888.9 |

EXAMPLE V

Conjugate Purity and In Vivo Toxicity

The purity of both 260F9-PL-rRTA and 260F9-IT-rRTA were analyzed by non-reducing SDS-PAGE gel and staining with Fast Green and gel scanning. In addition, endotoxin levels were assayed to be approximately 1-10 ng endotoxin/mg conjugate, as determined by the limulus amebocyte lysate (LAL) assay described by Watson et al., eds., *Proceedings of an International Conference on Endotoxin Standards and Limulus Amebocyte Lysate Use with Parenteral Drugs*, Alan R. Liss, Inc., New York (1982), the disclosure of which is incorporated herein by reference.

In vivo toxicity in mice was then tested. Three different groups of mice (3 mice/group) were given single-dose injections of 0, 4.25, 8.5 and 17.0 mg/kg of 260F9-PL-rRTA. The mice died in all three groups receiving conjugate giving a minimum lethal dose where 100% of the animals die (LD$_{100}$) of 4.25 mg/kg. This is in contrast with 260F9-IT-rRTA, which has a lethal dose where 50% of the animals die (LD50) of around 8.5 mg/kg. The conjugate with the protected linker was therefore found to be much more lethal.

EXAMPLE VI

In Vivo Behavior Of Conjugates Made Using The Protected Linker

In Vivo Stability of Conjugate

The in vivo stability of the conjugate with the protected linker (260F9-PL-rRTA) was compared to the iminothiolane-linked conjugate (260F9-IT-rRTA). Both conjugates were synthesized using 260F9 antibody internally labeled with $^{35}$S methionine. Nude mice were injected with 3.5 ug of the labled immunoconjugate and at the indicated times, sacrificed. Plasma samples were then analyzed on a 5% to 10% gradient SDS-PAGE gel and autoradiographed.

Figure 5:
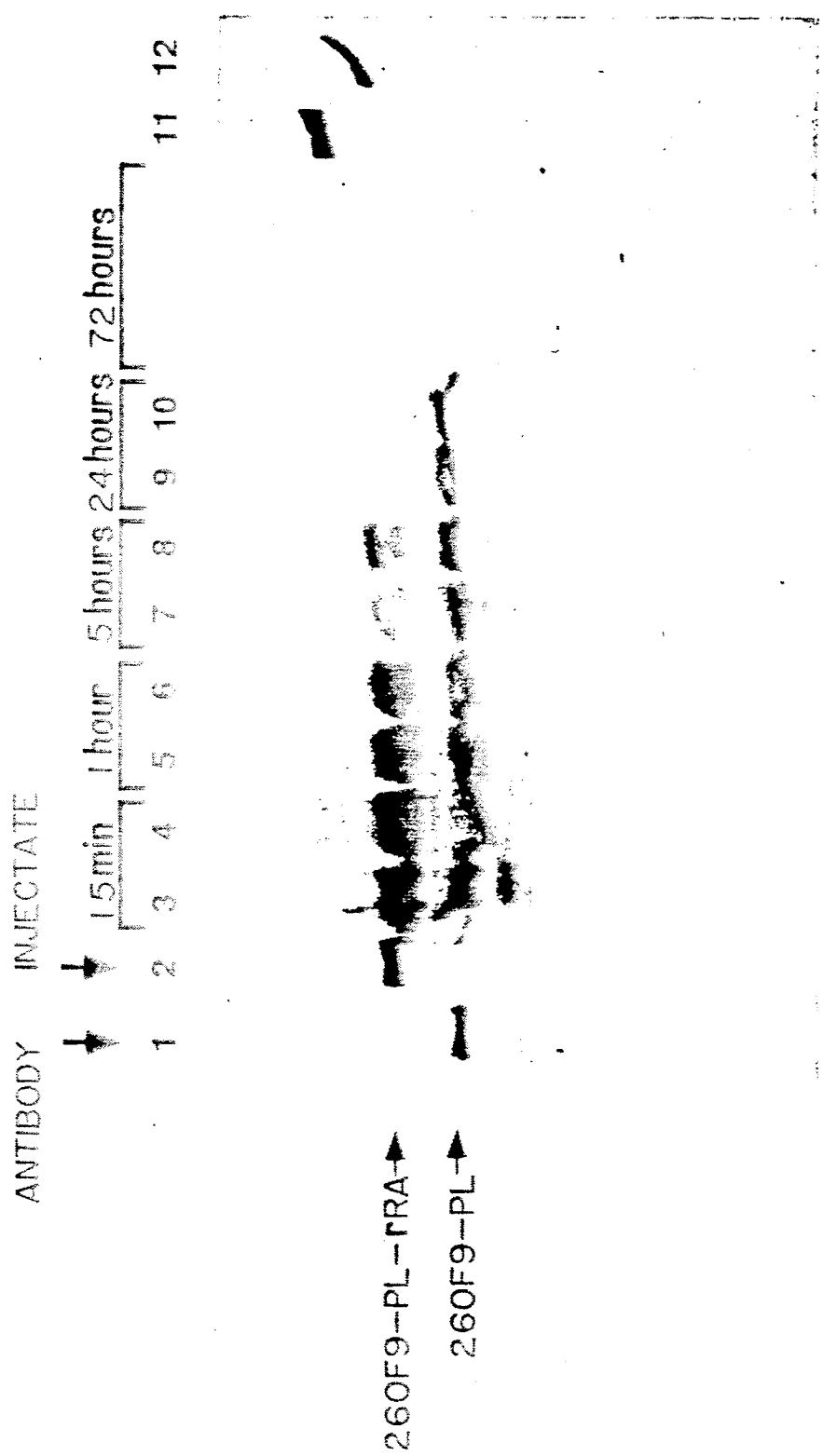
FIG. 5 is an autoradiograph of an SDS-PAGE gel showing the in vivo stability of $^{35}S$ methionine labeled 260F9-IT-rRTA.
Figure 6A:
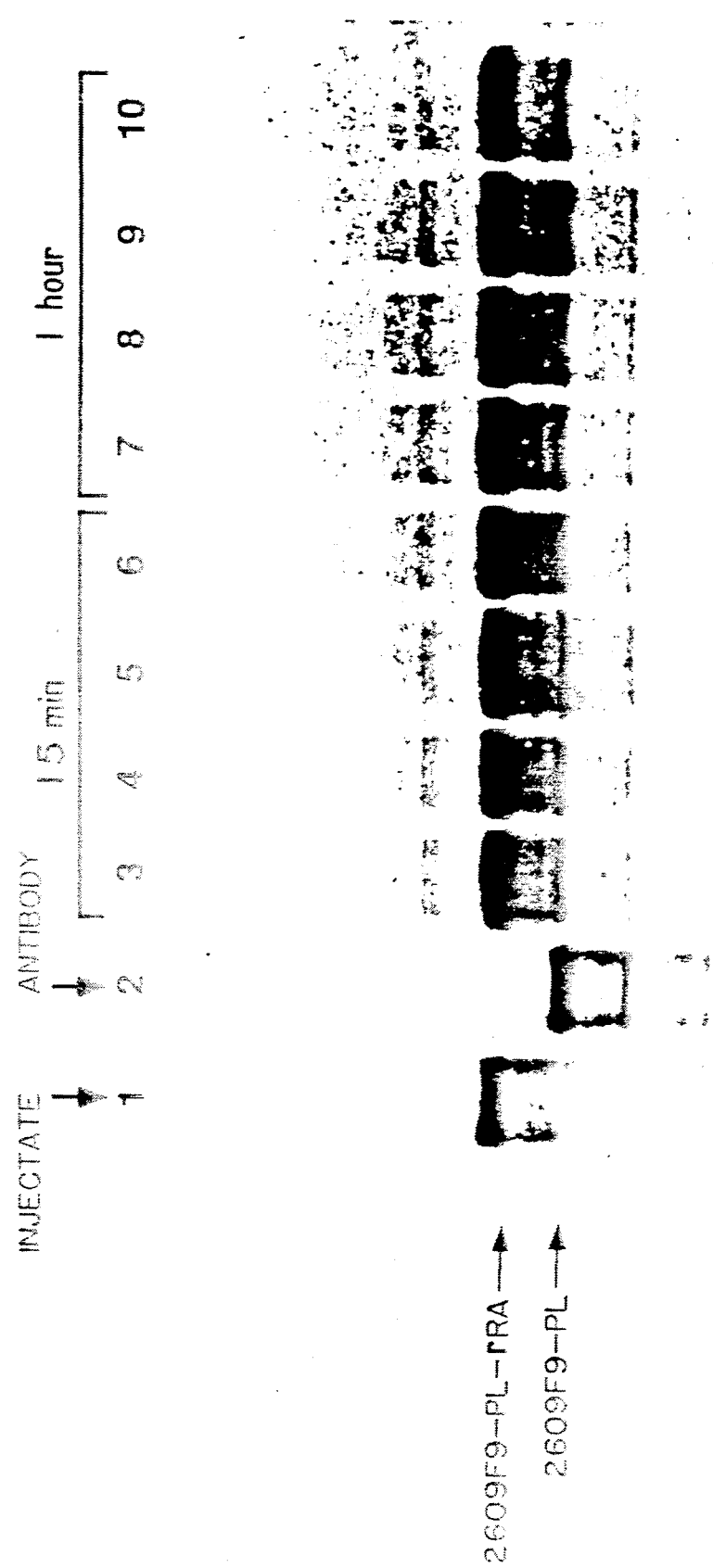
FIGS. 6(a)-(d) are autoradiographs of SDS-PAGE gels showing the in vivo stability of $^{35}S$ methionine labeled 260F9-PL-rRTA.
Figure 6B:
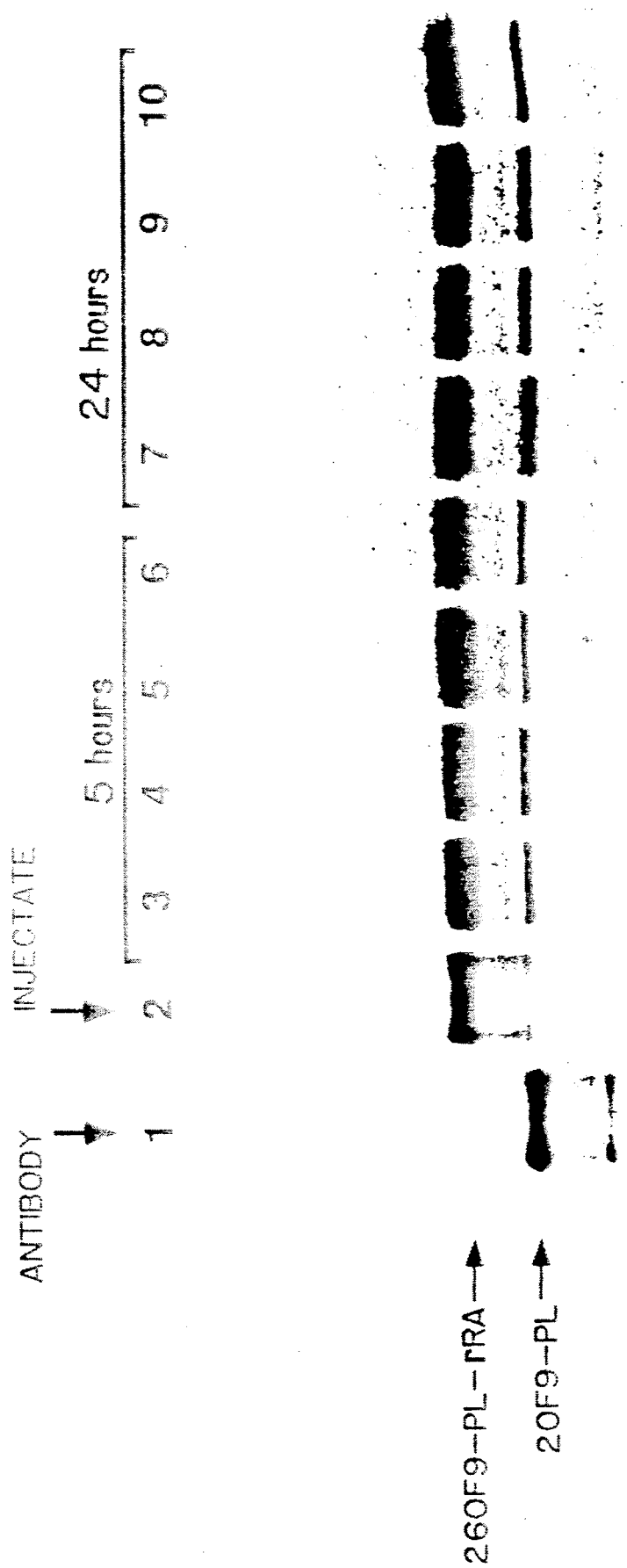
Figure 6C:
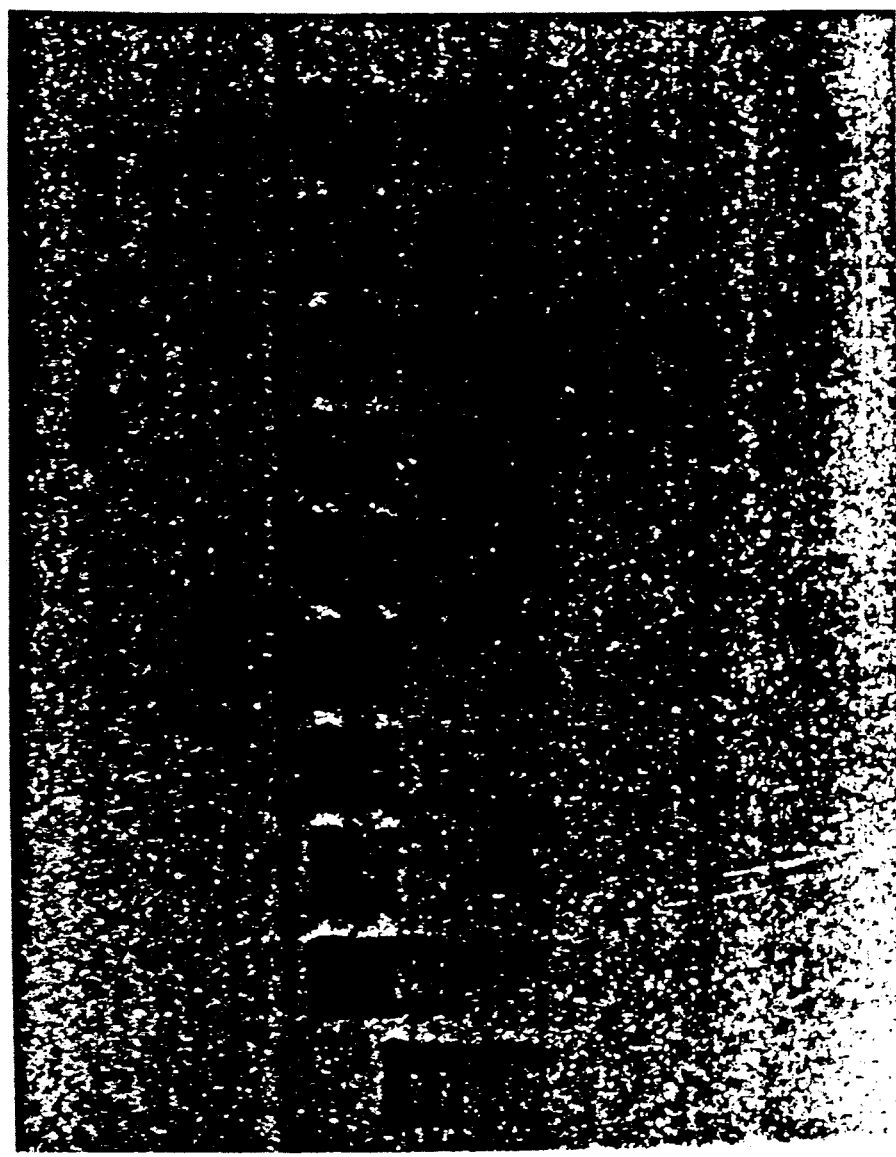
Figure 6D:
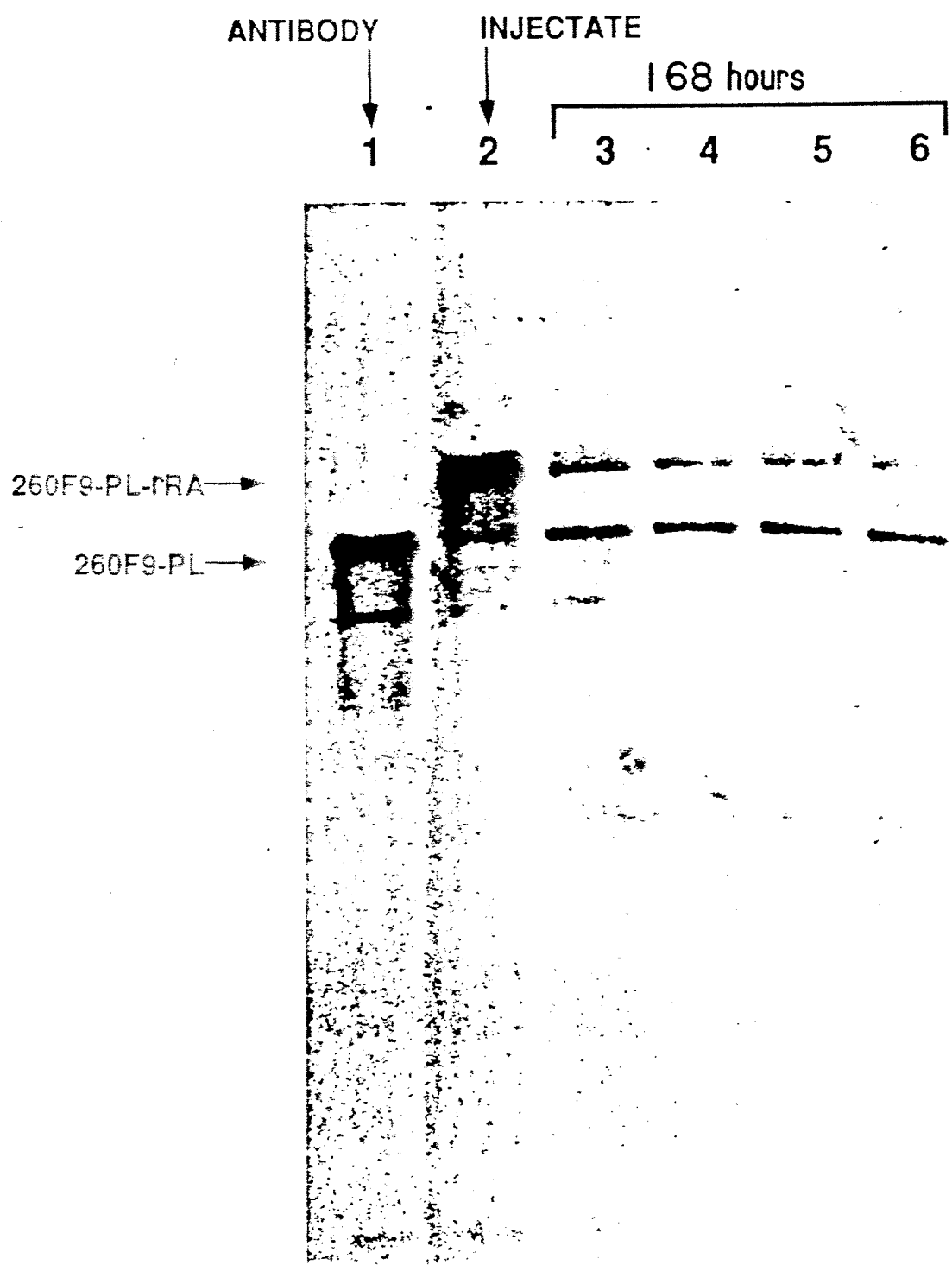

FIG. 5 is an autoradiograph which shows that for the case of the 2-iminothiolane-linked conjugate, very little intact material remains after 24 hours.

FIGS. 6(a)-(d) are a series of autoradiographs which show the protected-linker containing immunoconjugate to be intact after day 7. The presence of free antibody most likely represents the breakdown of a subpopulation of conjugate which occurs at early times since the level of antibody does not increase as it does with the iminothiolane-linked conjugate as seen in FIG. 5.

MX-1 Tumor Model

The MX-1 Tumor Model, as described by Ovejera, A. A. et al. (1978) *Annals of Clinical and Laboratory Science*, 8:51 and which is incorporated herein by reference, was used to study and compare the tumor growth inhibition and killing activity of 260F9-PL-rRTA and 260F9-IT-rRTA.

Nude mice (5-10/group) were implanted with MX-1 human breast tumors subcutaneously on day 7. After the tumor was allowed to grow 7 days (day) treatment was begun in which the mice were injected with the appropriate dose of immunoconjugate on day 0, 2, 4, 6, 8 and 10. The volume of the tumor was measured on days 0, 3, 7, 10 and 14.

The data in Tables 3(a)-(c) is from 3 respective experiments showing for each particular dosage of immunoconjugate; the average change in body weight of the test group (δBW), the number of deaths, the average change in tumor volume (δTV) and the percent tumor growth inhibition (% TGI).

TABLE 3(a)

| Group | Dose (UG) | ΔBW | Deaths | ΔTV | % TGI |
|---|---|---|---|---|---|
| PBS Control | — | 1.06 | 0/10 | 14.3 | 0 |
| 260F9-IT-rRTA | 3.5 | 1.05 | 1/10 | 10.1 | 23 |
| 260F9-IT-rRTA | 7.0 | 1.03 | 5/10 | 5.2 | 62 |
| 260F9-PL-rRTA | 1.75 | 1.04 | 6/10 | 2.6 | 81 |
| 260F0-PL-rRTA | 3.5 | 1.04 | 9/10 | 1.7 | 88 |

TABLE 3(b)

| Group | Dose (UG) | ΔBW | Deaths | ΔTV | % TGI |
|---|---|---|---|---|---|
| PBS Control | — | 1.09 | 0/5 | 17.4 | 0 |
| 260F9-IT-rRTA | 7.0 | 1.08 | 3/5 | 6.2 | 64 |
| 260F9-PL-rRTA | 0.175 | 1.10 | 0/5 | 12.7 | 27 |
| 260F9-PL-rRTA | 0.58 | 1.07 | 1/5 | 1.84 | 89 |
| 260F0-PL-rRTA | 1.75 | 0.74 | 4/5 | 0.48 | 97 |

TABLE 3(c)

| Group | Dose (UG) | ΔBW | Deaths | ΔTV | % TGI |
|---|---|---|---|---|---|
| PBS Control | — | 1.09 | 0/10 | 11.3 | 0 |
| 260F9-IT-rRTA | 3.5 | 1.03 | 1/10 | 9.6 | 38 |
| 260F9-IT-rRTA | 7.0 | 0.99 | 0/10 | 3.0 | 73 |
| 260F9-PL-rRTA | 3.5 | .90 | 3/10 | 1.1 | 91 |
| 260F9-PL-rRTA | 7.0 | 1.00 | 7/10 | 0.6 | 94 |

The greatest efficacy with acceptable toxicity for 260F9-PL-rRTA was with a dosage of 0.58 ug/kg, shown in Table 3(b). This is greater efficacy and even less toxicity than the 12 fold higher dosage of 7.0 ug/kg used for 260F9-IT-rRTA. In addition, at the 1.75 ug dose of 260F9-PL-rRTA shown in Table 3(b), the tumor of the one surviving mouse remained at 50% of the size at injection even out at day 21.

Figure 7:
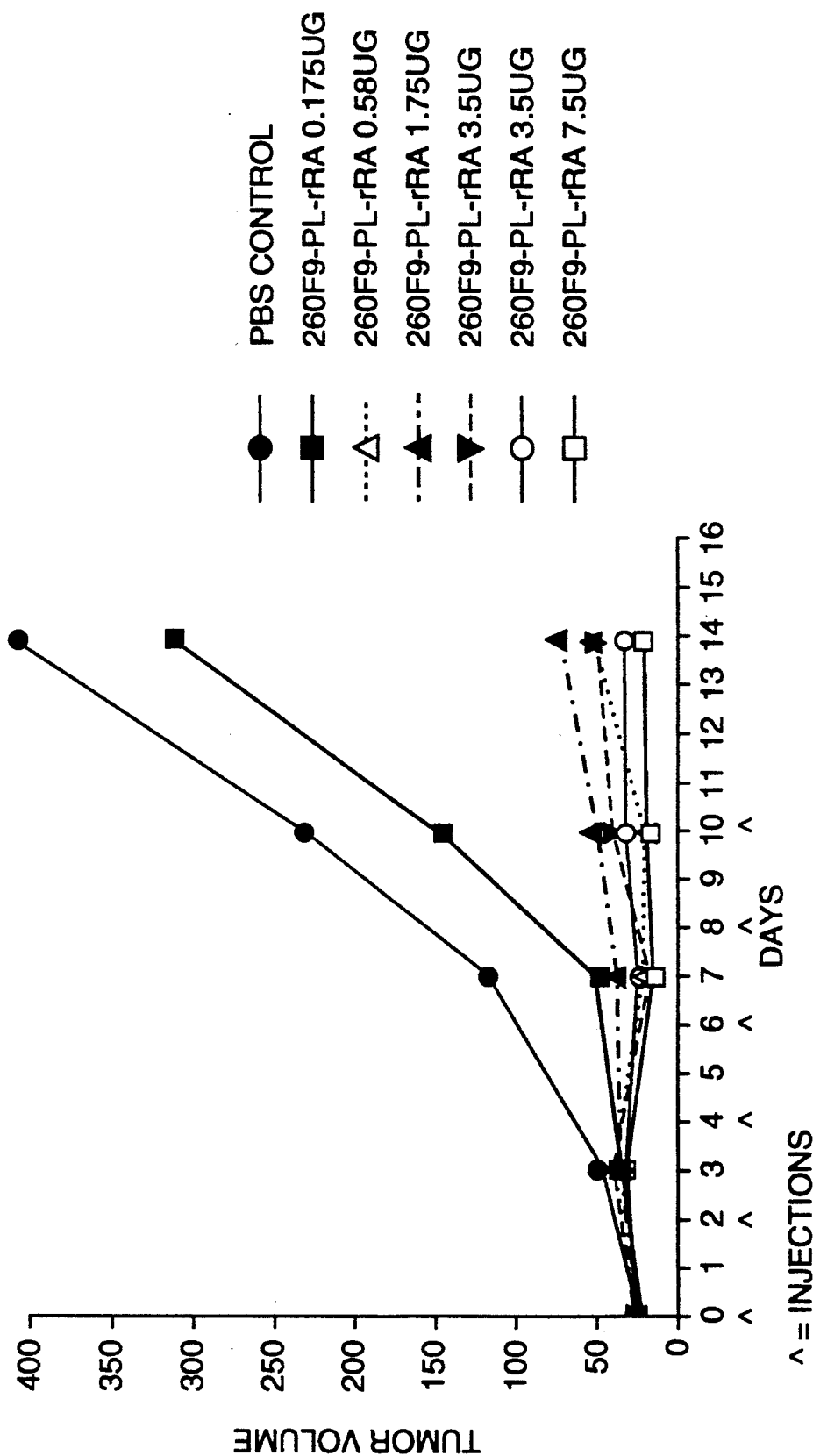
FIG. 7 is a graphic illustration showing tumor volume over time in response to 260F9-PL-rRTA and 260F9-IT-rRTA dose in the MX-1 tumor model.

The improved efficacy of the protected-linker containing immunoconjugate over the 2-iminothiolane linked conjugate is shown in FIG. 7 where the data of Table 3(a)-(c) is graphically illustrated. Tumor volume decreases over time showing a dose like response with 260F9-PL-rRTA being much more efficious than 260F9-IT-rRTA.

Pharmacokinetic Parameters

The total body clearance (TBC) of 260F9-PL-rRTA was compared to that of 260F9-IT-rRTA and a similar conjugate, 260F9-SMCC-rRTA. Conjugates using SMCC have a non-reducible cross-linker. The synthesis of SMCC (succinimidyl 4-(N-malaimidomethyl)cyclohexane-1-carboxylate is described by Yoshitaki, et al. *European J. Biochem.*, 101:395-399 (1979), the disclosure of which is incorporated herein by reference. The pharmacokinetic parameters of the three conjugates were compared in nude mice and Craig Dawley (CD) rats.

Nude Mice

269F9-IT-($^{35}$S)rRTA and 260F9-SMCC-($^{35}$S)rRTA were internally labeled in the rRTA portion and ($^{35}$S) 260F9-PL-rRTA was internally labeled in the antibody portion. Mice (4/group) were injected with the labeled conjuugate and at the indicated times. sacrificed to determine the amount of intact conjugate in the serum.

Intact IT and SMCC containing conjugates were determined directly by immunoprecipitation using antibody to 260F9. Intact PL containing conjugate was determined indirectly because immunoprecipitation detected labeled antibody, both intact and free. This was accomplished by scanning autoradiographs of non-reducing SDS-PAGE gel analysis of serum samples to determine the percent of total label in the intact conjugate. The amount of immunoprecipitated label was then multiplied by the percent of intact conjugate to obtain data points shown in FIG. 8.

CD Rats

Conjugate was injected into CD rats and the amount of intact conjugate was determined by sandwich ELISA assay. The capture-antibody was anti-rRTA and detection-antibody was horseradish peroxidase-labeled anti-mouse IgG. Intact 260F9-SMCC-($^{35}$S)rRTA was determined by both ELISA and immunoprecipitation to compare technique differences. Both methods gave similar results.

Figure 8:
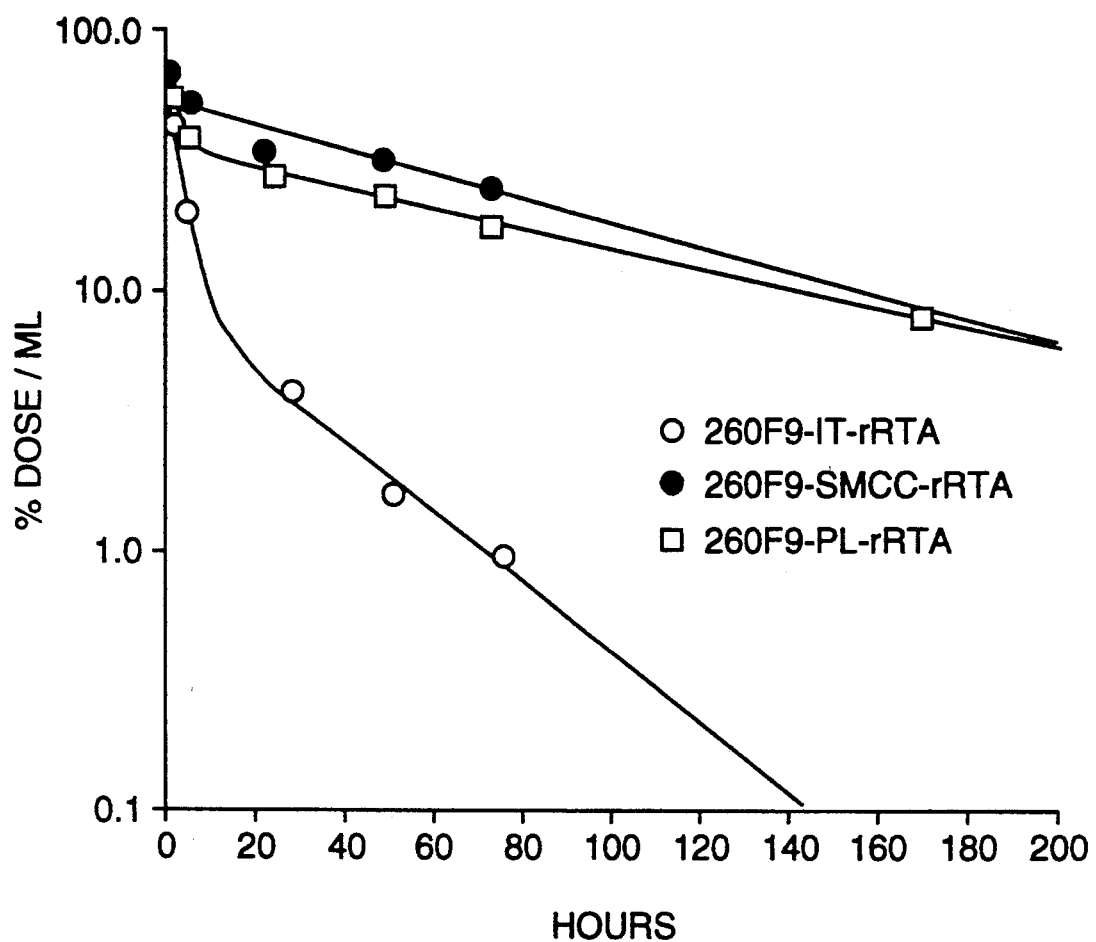
FIG. 8 is a graphic illustration showing the pharmacokinetic parameters in nude mice of 210F9-PL-rRTA, 260 F9-IT-rRTA and 260F9-SMCC-rRTA.

The pharmacokinetic parameters are shown in FIG. 8 (nude mice) and FIG. 9 (CD rats). Total body clearance and the $\beta$-phase half-life was determined using a curve stripping computer program; JANA (Dunne, A., (1985) *Comp. Meth. Prog. Biomed.*, 20:269–275), the disclosure of which is incorporated herein by reference.

The TBC and $\beta$-phase half-life for each conjugate in both nude mice and CD rats are shown in Table 4. The PL and SMCC containing conjugates show equivalent TBC rats and $\beta$-phase half-lives, indicating the hindered disulfide linker to be as stable as a non-reducible linker.

Relative to the IT linked conjugate, the hindred disulfide linked conjugate showed a 10-fold slower TBC rate in mice and a 2-fold slower rate in CDrats. In addition, T1/2 $\beta$-phase for the IT based conjugate was less than half that of the PL based conjugate in mice and a fourth of the value found in CD rats.

TABLE 4

Pharmacokinetic Parameters of 260F9 Immunoconjugates

| Sample | TBC Ml/Kg/Min. | T½ (Hours) $\beta$-Phase |
|---|---|---|
| Nude Mice | | |
| 260F9-IT-rRTA | 0.14 | 23 |
| 260F9-SMCC-rRTA | 0.014 | 64 |
| 260F9-PL-rRTA | 0.017 | 79 |
| 260F9 | | >200 |
| CD Rats | | |
| 260F9-IT-rRTA | 0.14 | 4.5 |
| 260F9-SMCC-rRTA | 0.06 | 22 |
| 260F9-PL-rRTA | 0.06 | 18 |
| 260F9 | | >1000 |

Deposits

The monoclonal-antibody-producing hybridomas listed below were deposited with the American Type Culture Collection (ATCC) or Invitro International Inc. (IVI) under the terms of the Budapest Treaty on the International Recognition of the Deposit of Microorganisms for the Purposes of Patent Procedure and the Regulations thereunder (Budapest Treaty). This assures maintenance of the viable culture for 30 years from date of deposit. The hybridomas will be made available by ATCC or IVI under the terms of the Budapest Treaty, and subject to an agreement between the assignee of this application, Cetus Corporation, and ATCC or IVI that assures unrestricted availability upon issuance of the pertinent U.S. patent. Availability of the deposited strains is not to be construed as a license to practice the invention in contravention of the rights granted under the authority of any government in accordance with its patent laws. The assignee has agreed that if the cell lines on deposit should die or be lost or destroyed when cultivated under suitable conditions, they will be promptly replaced on notification with a viable culture of the same cell line.

Each hybridoma designation listed in the left column of these tables corresponds to the monoclonal antibody cell line producing the designated monoclonal antibody.

| Hybridoma Antibody Designation | Deposit Date | ATCC Accession No. |
|---|---|---|
| 260F9 | 1/27/84 | HB 8488 |
| 113F1 | 1/27/84 | HB 8490 |
| 2G3 | 1/27/84 | HB 8491 |
| 280D11 | 1/27/84 | HB 8487 |
| 266B2 | 1/27/84 | HB 8486 |
| 245E7 | 1/27/84 | HB 8489 |
| 454C11 | 1/27/84 | HB 8484 |
| 33F8 | 1/9/85 | HB 8697 |
| 317G5 | 1/27/84 | HB 8484 |
| 520C9 | 1/8/85 | HB 8696 |
| 369F10 | 12/13/84 | HB 8682 |
| *260F9-1C9 | 11/7/84 | HB 8662 |
| 317G5 (CTCC 0055) | 12/28/84 | HB 8691 |
| 788G6 | 12/28/84 | HB 8692 |

| Hybridoma Antibody Designation | IVI Accession No. |
|---|---|
| 106A10 | 10060 |
| 452F2 | 10082 |
| 650E2 | 10083 |
| 741F8 | 10078 |
| 759E3 | 10079 |
| 9C6 | 10056 |
| 44B2 | 10068 |
| 44F4 | 10058 |
| 120H7 | 10061 |
| 200F9 | 10062 |
| 204F4 | 10071 |
| 219F3 | 10072 |
| 388D4 | 10065 |
| 421E8 | 10064 |
| 871E3 | 10084 |
| 451C3 | 10081 |
| 454A12 | 10075 |

*This clone is a progeny of 260F99 and was found to be a better antibody producer than 260F9.

In addition, the following plasmids were deposited with the ATCC on the indicated date under the conditions described above.

| Plasmid Designation | Deposit Date | ATCC Accession No. |
|---|---|---|
| pRA123 | 8/17/84 | 39799 |
| pRAL6/MC1000g | 9/4/84 | 39833 |
| pRTB704/MC1000g | 9/14/84 | 39865 |
| pFC5/MC1000g | 9/14/84 | 39864 |
| pRAP229 | 3/8/85 | 53408 |
| pTRP3 | 12/18/84 | 39946 |
| pPLOP | 12/18/84 | 39947 |
| pRT3 | 3/7/86 | 67027 |
| pRT17 | 3/7/86 | 67026 |
| pRT38 | 3/7/86 | 67025 |

The foregoing written specification is considered to be sufficient to enable one skilled in the art to practice the invention. The present invention is not to be limited in scope by the cell lines deposited, since the deposited embodiment is intended as a single illustration of one aspect of the invention and any cell lines that are functionally equivalent are within the scope of this invention.

The deposite of materials therein does not constitute an admission that the written description herein contained is inadequate to enable the practice of any aspect of the invention, including the best mode thereof, nor are the deposits to be construed as limiting the scope of the claims to the specific illustrations that they represent. Indeed, various modifications of the invention in addition to those shown and described herein will become apparent to those skilled in the art from the foregoing description and fall within the scope of the appended claims.

What is claimed is:

1. Compounds of the following general structure

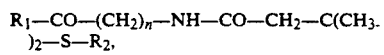

wherein $R_1$ is an activated ester leaving moiety; n is between 1 and 20; and, $R_2$ is H or a thiol blocking moiety.

2. The compound of claim 1 wherein $R_1$ is selected from the group consisting of

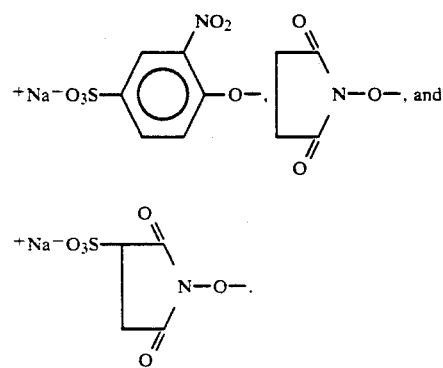

3. The compound of claim 1 wherein $R_2$ is selected from the group consisting of

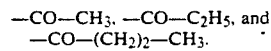

4. The compound of claim 1 wherein $R_1$ is

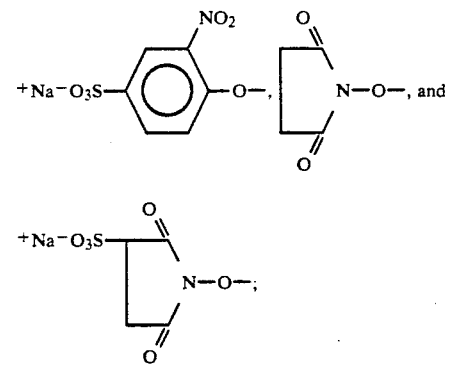

n is 2; and
$R_2$ is $CO-CH_3$.

5. The compound of claim 1 wherein $R_1$ is

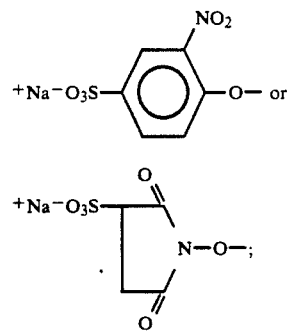

n is 2, and;
$R_2$ is $CO-CH_3$.

6. A compound of the following general formula:

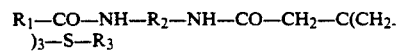

wherein $R_1$ is a thiol alkylating moiety, $R_2$ is an acyclic aliphatic spacer arm, and $R_3$ is a thiol blocking moiety.

7. The compound of claim 6 wherein $R_1$ is a compound selected from the group consisting of

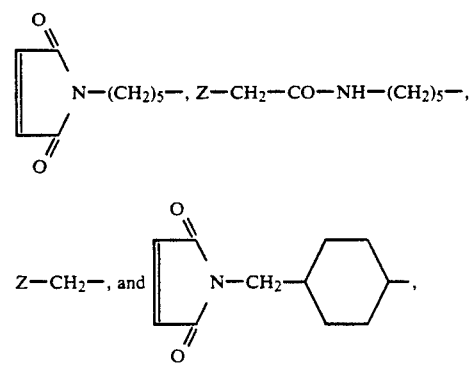

Z is a halogen selected from the group consisting of Cl, Br, and I;
$R_2$ is selected from the group consisting of

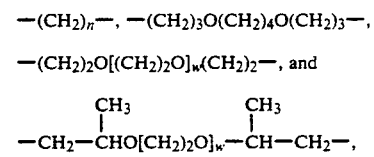

n is between 1 and 20, and
w is between 1 and 100; and,
$R_3$ is selected from the group consisting of

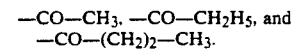

8. The compound of claim 7, wherein Z is selected from the group consisting of Cl, Br, and I; n is 6; w is between 1 and 5; and $R_3$ is $-CO-CH_3$.

9. The compound of claim 8 wherein n is 2; w is between 1 and about 5; Z is Br; and $R_3$ is $-CO-CH_3$.

* * * * *